United States Patent
Ziebol et al.

(10) Patent No.: US 10,159,829 B2
(45) Date of Patent: Dec. 25, 2018

(54) PACKAGING CONTAINER FOR ANTIMICROBIAL CAPS

(71) Applicant: Pursuit Vascular, Inc., Maple Grove, MN (US)

(72) Inventors: Robert J. Ziebol, Blaine, MN (US); Keith J. Modert, Vadnais Heights, MN (US); Matthew Case Ziebol, Maple Grove, MN (US)

(73) Assignee: Pursuit Vascular, Inc., Maple Grove, MN (US)

( * ) Notice: Subject to any disclaimer, the term of this patent is extended or adjusted under 35 U.S.C. 154(b) by 692 days.

(21) Appl. No.: 14/793,492

(22) Filed: Jul. 7, 2015

(65) Prior Publication Data

US 2016/0001058 A1 Jan. 7, 2016

Related U.S. Application Data

(63) Continuation of application No. 14/720,378, filed on May 22, 2015, now Pat. No. 9,352,142, which is a
(Continued)

(51) Int. Cl.
*B65D 75/00* (2006.01)
*A61M 39/20* (2006.01)
(Continued)

(52) U.S. Cl.
CPC ............. *A61M 39/20* (2013.01); *A61B 50/30* (2016.02); *A61L 2/186* (2013.01); *A61L 29/08* (2013.01);
(Continued)

(58) Field of Classification Search
USPC ............... 206/231, 205, 206, 207, 493, 443; 220/4.27, 4.21, 4.24, 4.26, 23.8, 23.2,
(Continued)

(56) References Cited

U.S. PATENT DOCUMENTS

| 559,697 A | * | 5/1896 | Gallagher | ................ B65D 1/04 |
| | | | | 215/6 |
| 975,939 A | * | 11/1910 | Edwards | ................... A45F 3/16 |
| | | | | 206/547 |

(Continued)

FOREIGN PATENT DOCUMENTS

| CN | 102202716 | 9/2011 |
| CN | 103796704 | 5/2014 |

(Continued)

OTHER PUBLICATIONS

Notice of Allowance for U.S. Appl. No. 14/720,378, dated Apr. 20, 2016 (11 pages).
(Continued)

*Primary Examiner* — Jacob K Ackun
(74) *Attorney, Agent, or Firm* — Pauly, DeVries Smith & Deffner LLC

(57) ABSTRACT

Systems, methods, and articles for providing an antimicrobial composition to the proximal elements of a trans-dermal catheter and into the lumen of the transdermal catheter are disclosed. In an embodiment, an antimicrobial composition on surface a cap element transfers antimicrobial to the proximal end of the transdermal catheter. The system comprises an elongate member configured for insertion into a lumen of a catheter, the elongate member containing an antimicrobial.

3 Claims, 30 Drawing Sheets

Related U.S. Application Data continuation of application No. 13/915,605, filed on Jun. 11, 2013, now Pat. No. 9,078,992, which is a continuation-in-part of application No. 13/834,755, filed on Mar. 15, 2013, now Pat. No. 8,622,996, which is a continuation-in-part of application No. 13/752,385, filed on Jan. 28, 2013, now Pat. No. 8,622,995, said application No. 14/720,378 is a continuation-in-part of application No. 13/547,572, filed on Jul. 12, 2012, now Pat. No. 9,849,276, and a continuation-in-part of application No. 12/605,966, filed on Oct. 26, 2009, now Pat. No. 9,072,868.

(60) Provisional application No. 61/752,959, filed on Jan. 15, 2013, provisional application No. 61/506,979, filed on Jul. 12, 2011, provisional application No. 61/108,716, filed on Oct. 27, 2008.

(51) Int. Cl.
| | | |
|---|---|---|
| *A61M 25/00* | (2006.01) | |
| *A61L 29/08* | (2006.01) | |
| *A61L 2/18* | (2006.01) | |
| *A61L 29/16* | (2006.01) | |
| *A61L 31/16* | (2006.01) | |
| *A61B 50/30* | (2016.01) | |
| *A61M 5/00* | (2006.01) | |
| *A61M 39/16* | (2006.01) | |
| *A61M 1/36* | (2006.01) | |

(52) U.S. Cl.
CPC .............. *A61L 29/16* (2013.01); *A61L 31/16* (2013.01); *A61M 25/0017* (2013.01); *A61M 25/0043* (2013.01); *A61B 2050/3008* (2016.02); *A61L 2202/24* (2013.01); *A61L 2300/206* (2013.01); *A61L 2300/404* (2013.01); *A61L 2300/606* (2013.01); *A61L 2420/02* (2013.01); *A61M 1/3661* (2014.02); *A61M 5/001* (2013.01); *A61M 25/002* (2013.01); *A61M 39/162* (2013.01); *A61M 39/165* (2013.01); *A61M 2025/0018* (2013.01); *A61M 2025/0019* (2013.01); *A61M 2025/0056* (2013.01); *A61M 2209/10* (2013.01)

(58) Field of Classification Search
USPC .................. 220/500, 503, 504, 506, 916
See application file for complete search history.

(56) References Cited

U.S. PATENT DOCUMENTS

| | | | | |
|---|---|---|---|---|
| 1,445,642 | A * | 2/1923 | O'Neill | B65D 81/3288 220/504 |
| 3,262,448 | A | 7/1966 | Ring et al. | |
| 3,595,241 | A | 7/1971 | Sheridan | |
| 3,977,517 | A * | 8/1976 | Kadlecik | A45C 11/005 206/205 |
| 4,078,686 | A * | 3/1978 | Karesh | B65D 25/04 215/12.1 |
| 4,331,783 | A | 5/1982 | Stoy | |
| 4,337,327 | A | 6/1982 | Stoy | |
| 4,369,294 | A | 1/1983 | Stoy | |
| 4,370,451 | A | 1/1983 | Stoy | |
| 4,379,874 | A | 4/1983 | Stoy | |
| 4,420,589 | A | 12/1983 | Stoy | |
| 4,440,207 | A * | 4/1984 | Genatempo | A61L 31/16 150/154 |
| 4,446,967 | A | 5/1984 | Halkyard | |
| 4,559,043 | A | 12/1985 | Whitehouse et al. | |
| 4,624,664 | A | 11/1986 | Peluso et al. | |
| 4,631,188 | A | 12/1986 | Stoy et al. | |
| 4,705,790 | A | 11/1987 | Hubele et al. | |
| 4,769,013 | A | 9/1988 | Lorenz et al. | |
| 4,808,158 | A | 2/1989 | Kreuzer et al. | |
| 4,889,255 | A * | 12/1989 | Schiemann | B65D 1/04 215/382 |
| 4,894,056 | A | 1/1990 | Bommarito | |
| 5,015,238 | A | 5/1991 | Solomon et al. | |
| 5,071,413 | A | 12/1991 | Utterberg et al. | |
| 5,154,920 | A | 10/1992 | Flesher et al. | |
| 5,240,675 | A | 8/1993 | Wilk et al. | |
| 5,297,310 | A | 3/1994 | Cox et al. | |
| 5,330,899 | A * | 7/1994 | DeVaughn | B01L 3/5085 206/363 |
| 5,337,730 | A | 8/1994 | Maguire | |
| 5,366,505 | A | 11/1994 | Farber | |
| 5,370,640 | A | 12/1994 | Kolff | |
| 5,375,589 | A | 12/1994 | Bhatta | |
| 5,407,807 | A | 4/1995 | Markus | |
| 5,409,012 | A | 4/1995 | Sahatjian | |
| 5,628,733 | A | 5/1997 | Zinreich et al. | |
| 5,782,808 | A | 7/1998 | Folden | |
| 5,902,631 | A | 5/1999 | Wang et al. | |
| 5,951,519 | A | 9/1999 | Utterberg | |
| 6,045,623 | A | 4/2000 | Cannon | |
| 6,059,107 | A | 5/2000 | Nøsted et al. | |
| 6,071,413 | A | 6/2000 | Dyke et al. | |
| 6,105,812 | A * | 8/2000 | Riordan | B65D 1/04 215/6 |
| 6,183,450 | B1 | 2/2001 | Lois | |
| 6,232,406 | B1 | 5/2001 | Stoy | |
| 6,237,800 | B1 * | 5/2001 | Barrett | A01K 7/00 215/312 |
| 6,409,716 | B1 | 6/2002 | Sahatjian et al. | |
| 6,444,318 | B1 | 9/2002 | Guire et al. | |
| 6,468,259 | B1 * | 10/2002 | Loretti | B29C 66/73921 206/828 |
| 6,605,294 | B2 | 8/2003 | Sawhney | |
| 6,605,751 | B1 | 8/2003 | Gibbins et al. | |
| 6,634,498 | B2 | 10/2003 | Kayerød et al. | |
| 6,725,492 | B2 | 4/2004 | Moore et al. | |
| 7,097,850 | B2 | 8/2006 | Chappa et al. | |
| 7,195,615 | B2 | 3/2007 | Tan | |
| 7,442,402 | B2 | 10/2008 | Chudzik et al. | |
| 7,922,701 | B2 | 4/2011 | Buchman et al. | |
| 8,146,757 | B2 * | 4/2012 | Abreu | B65D 1/0223 215/370 |
| 8,500,717 | B2 | 8/2013 | Becker | |
| 8,622,995 | B2 | 1/2014 | Ziebol et al. | |
| 8,622,996 | B2 | 1/2014 | Ziebol et al. | |
| 9,022,984 | B2 | 5/2015 | Ziebol et al. | |
| 9,072,868 | B2 | 7/2015 | Ziebol et al. | |
| 9,078,992 | B2 | 7/2015 | Ziebol et al. | |
| 9,352,142 | B2 | 5/2016 | Ziebol et al. | |
| 9,849,276 | B2 | 12/2017 | Ziebol et al. | |
| 2004/0034329 | A1 | 2/2004 | Mankus et al. | |
| 2004/0156908 | A1 | 8/2004 | Polaschegg et al. | |
| 2005/0098527 | A1 * | 5/2005 | Yates, III | B29C 49/0073 215/6 |
| 2005/0124970 | A1 | 6/2005 | Kunin et al. | |
| 2005/0171493 | A1 | 8/2005 | Nicholls | |
| 2005/0220882 | A1 | 10/2005 | Pritchard et al. | |
| 2005/0267421 | A1 | 12/2005 | Wing | |
| 2005/0288551 | A1 | 12/2005 | Callister et al. | |
| 2006/0024372 | A1 | 2/2006 | Utterberg et al. | |
| 2006/0206178 | A1 | 9/2006 | Kim | |
| 2008/0132880 | A1 | 6/2008 | Buchman | |
| 2008/0172007 | A1 | 7/2008 | Bousquet | |
| 2008/0319423 | A1 | 12/2008 | Tanghoj et al. | |
| 2009/0062766 | A1 | 3/2009 | Howlett et al. | |
| 2009/0137969 | A1 | 5/2009 | Colantonio et al. | |
| 2009/0205151 | A1 | 8/2009 | Fisher et al. | |
| 2009/0247485 | A1 | 10/2009 | Ahmed et al. | |
| 2010/0106102 | A1 | 4/2010 | Ziebol et al. | |
| 2010/0106103 | A1 | 4/2010 | Ziebol et al. | |
| 2010/0143427 | A1 | 6/2010 | King et al. | |
| 2011/0030726 | A1 | 2/2011 | Vaillancourt et al. | |
| 2012/0022469 | A1 | 1/2012 | Alpert et al. | |
| 2013/0039953 | A1 | 2/2013 | Dudnyk et al. | |

(56) References Cited

U.S. PATENT DOCUMENTS

| | | | | |
|---|---|---|---|---|
| 2013/0134161 A1* | 5/2013 | Fogel | ................ | B65D 21/0209 220/23.83 |
| 2013/0144258 A1 | 6/2013 | Ziebol et al. | | |
| 2013/0184679 A1 | 7/2013 | Ziebol et al. | | |
| 2013/0204231 A1 | 8/2013 | Ziebol et al. | | |
| 2013/0274686 A1 | 10/2013 | Ziebol et al. | | |
| 2014/0042116 A1* | 2/2014 | Shen | ................ | B65D 21/0204 215/6 |
| 2015/0343174 A1 | 12/2015 | Ziebol et al. | | |

FOREIGN PATENT DOCUMENTS

| | | |
|---|---|---|
| DE | 3515665 | 5/1986 |
| EP | 1442753 | 2/2007 |
| EP | 1813293 | 8/2007 |
| WO | 2006102756 | 10/2006 |
| WO | 2010062589 | 6/2010 |
| WO | 2013009998 | 1/2013 |

OTHER PUBLICATIONS

Second Office Action for Chinese Patent Application No. 201280042898. 8, dated Apr. 5, 2016 (11 pages) with English translation.
Communication Pursuant to Article 94(3) EPC for European Patent Application No. 09829587.6 dated Nov. 29, 2012 (5 pages).
File History for U.S. Appl. No. 12/605,963 downloaded Mar. 4, 2016 (271 pages).
International Preliminary Report on Patentability for PCT/US2009/062190, dated May 12, 2011 (6 pages).
International Preliminary Report on Patentability for PCT/US2012/046496, dated Jan. 23, 2014, (8 pages).
International Search Report and Written Opinion for PCT/US2009/062190, dated May 26, 2010 (11 pages).
International Search Report and Written Opinion for PCT/US2012/046496, dated Jan. 28, 2013 (12 pages).
Non-Final Office Action for Chinese Patent Application No. 201280042898.8, dated May 21, 2015 (15 pages) with English Translation.
Office Action for Chinese Application No. 200980142920.4, dated Dec. 4, 2012 (9 pages).
Response to Communication Pursuant to Article 94(3) EPC for European Patent Application No. 098295876, dated Nov. 29, 2012 and filed with the EPO Mar. 18, 2013 (7 pages).
Final Office Action for U.S. Appl. No. 13/547,572 dated Feb. 17, 2017 (13 pages).
Response to Noting a Loss of Rights pursuant to Rule 112(1) EPC for European Patent Application No. 12810890.9 filed with the EPO Nov. 1, 2016 (25 pages).
Extended European Search Report for European Patent Application No. 12810890.9 dated Dec. 9, 2015 (11 pages).
Non-Final Office Action for U.S. Appl. No. 13/547,572 dated Jul. 21, 2016 (22 pages).
Office Action for Canadian Patent Application No. 2,841,832 dated Mar. 14, 2018 (3 pages).

* cited by examiner

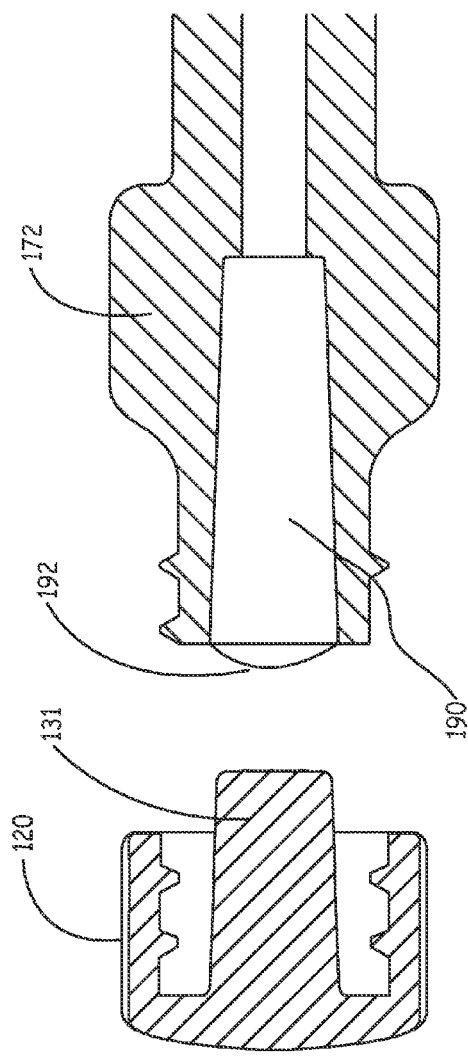
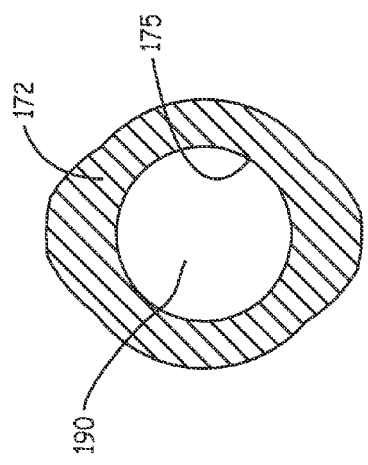
FIG. 11A
FIG. 11B

PACKAGING CONTAINER FOR ANTIMICROBIAL CAPS

This application is a continuation of U.S. Utility application Ser. No. 14/720,378, filed May 22, 2015, which is a continuation of U.S. Utility application Ser. No. 13/915,605, filed Jun. 11, 2013, which is a continuation-in-part of U.S. Utility application Ser. No. 13/834,755 filed Mar. 15, 2013, now U.S. Pat. No. 8,622,996, issued on Jan. 7, 2014; which is a continuation-in-part of Ser. No. 13/752,385, filed Jan. 28, 2013, now U.S. Pat. No. 8,622,995, issued on Jan. 7, 2014; which claims the benefit of U.S. Provisional Application No. 61/752,959, filed Jan. 15, 2013. This application is also a continuation-in-part of Ser. No. 13/547,572, filed Jul. 12, 2012, which claims the benefit of 61/506,979, filed Jul. 12, 2011, and is a continuation-in-part of Ser. No. 12/605,966, filed Oct. 26, 2009, which claims the benefit of U.S. Provisional Application No. 61/108,716, filed on Oct. 27, 2008, the contents of which are herein incorporated by reference.

FIELD OF THE INVENTION

The present invention relates to medical device systems, methods, and articles for providing antimicrobial properties in-situ to the proximal end of catheters and drainage tubes.

BACKGROUND OF THE INVENTION

Hemodialysis catheters allow patients with renal disease to have toxins removed from their bloodstream. Without the use of catheters, many of these patients would not survive. However, long-term hemodialysis catheters have a serious drawback in that a significant percentage of catheters fail due to infection, resulting in elevated mortality rates and large annual healthcare costs associated with treatment. Furthermore, bloodstream infections are a leading cause of death in the United States, and many of those infections are attributable to vascular access devices such as hemodialysis catheters. The mortality rate associated with such infections is considerable.

Therefore, a need exists for a manner in which infections relating to long-term hemodialysis catheters can be reduced.

SUMMARY OF THE INVENTION

The present application is directed in part to a device for delivering an antimicrobial composition to the proximal end of a trans-dermal catheter, the device comprising a sealing cover configured for placement over the proximal end of a catheter; and an antimicrobial composition positioned on at least a portion of the interior of the sealing cover.

The present application is also directed, in various implementations, to a device for delivering an antimicrobial composition into the lumen of a trans-dermal catheter and to proximal elements of the transdermal catheter. The device comprises a cover for installing over the end of a catheter, the cover having a protrusion configured for insertion into the proximal end of the catheter. An antimicrobial composition is positioned to be delivered into the catheter and/or at the end of the catheter (such as on the threads of the catheter). At least a portion of the antimicrobial composition is delivered to the exterior of the proximal end of the catheter upon insertion of the protrusion on the sealing cover into the proximal end of the catheter.

The application is further directed in certain implementations to a method of applying an antimicrobial composition to the proximal end of a trans-dermal catheter. The method includes providing a transdermal catheter; filling at least a portion of the proximal end of the transdermal catheter with a lock solution; clamping the transdermal catheter near its proximal end to restrict flow of the lock solution into the distal end of the transdermal catheter; and inserting a protrusion on the interior of a cover into the proximal end of the transdermal catheter. The protrusion sufficiently displaces lock solution so as to have the lock solution flow from the proximal end of the catheter, thereby delivering antimicrobial composition to the exterior of the catheter.

This summary is not intended to be limiting of the invention. The invention is further described in the following detailed description and claims.

BRIEF DESCRIPTION OF THE DRAWINGS

The invention may be more completely understood in connection with the following drawings, in which:

FIG. 11A is a side cross section view of a sealing cover made in accordance with an implementation of the invention, the sealing cover prior to being inserted into a catheter.

FIG. 11B is an end cross section view of the catheter of FIG. 11A.

Figure 1A:
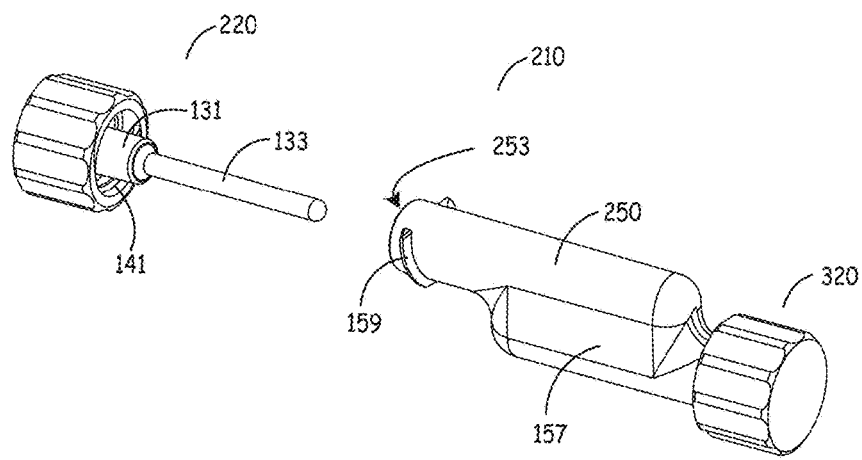
FIG. 1A is a perspective view of a packaging container with two sealing covers made in accordance with an implementation of the invention. One sealing cover is placed in the packaging container; the other sealing cover removed from the packaging container.

It will be noted that in some cross sectional figures the illustrations have been simplified, such as removal of the background threads on the sealing cover so as to make the various aspects of the invention more apparent. See, for example, FIG. 11A where those background threads are removed, compared to FIG. 3B where the background threads are depicted.

DETAILED DESCRIPTION OF THE INVENTION

The present invention relates to devices, systems, and methods for controlling, preventing and eliminating infectious organisms in medical devices, such as catheters and drainage tubes, and preventing the organisms from entering the bloodstream. The devices, systems, and methods deliver antimicrobial compositions into the lumen and near the entry region of catheters and drainage tubes. In particular, the present application is directed to a device for delivering an antimicrobial composition to the proximal end of a transdermal catheter, the device comprising a sealing cover configured for placement over the proximal end of a catheter; and an antimicrobial composition positioned on the sealing cover so as to be delivered to the proximal end of the catheter such that the antimicrobial composition is retained in the proximal end of the catheter and/or is released onto external portions of the proximal end of the catheter.

Research and development into preventing catheter-related bloodstream infections (CRBSI) over the last twenty years has been focused on methods for killing the bacteria along the inside and outside length of the catheter. This research has resulted in success at reducing the incidence of CRBSI in some catheter types. For instance, commercially successful antimicrobial coated catheters have resulted in a decrease in the incidence of infection in applications that use short-term (non-tunneled) catheters.

However, these coatings wash off with use and therefore are not effective for long-term applications. The use of long-term (tunneled, cuffed) hemodialysis catheters result in approximately 2.3 bloodstream infections every 1000 catheter days. Expressed another way, a patient dialyzing with a hemodialysis catheter can expect to develop a bloodstream infection, on average, every 14 months.

The present invention prevents, reduces and can even eliminate infectious organisms from the entry region of a catheter or tube, and from within the inner luminal surface of a catheter or other similar medical devices by providing a means for the prolonged presence of an antimicrobial composition and/or providing a means for periodically scrubbing the entry region and/or lumen of the catheter or other medical device to remove the infectious organisms and the biofilm in which infectious organisms proliferate.

The present invention includes methods and devices for killing organisms and preventing organism proliferation and biofilm formation in catheters so that organisms aren't able to exit the catheter and enter the bloodstream of a patient. The article of the present invention prevents, or reduces the number of, organisms reaching the bloodstream by employing any or all of the following example prevention methods: 1) physically blocking migration of organisms outside the catheter, 2) killing organisms along the threads, end face and luer connector (inside and outside of the connector) at the proximal end (outside of the body) of the catheter using an antimicrobial composition, and/or 3) killing organisms within a confined region of the catheter using an antimicrobial composition and/or a physical barrier in the catheter lumen. A fourth mode of action, scrubbing the catheter wall (to physically remove organisms adhered to the interior wall section upon removing the sealing cover from the catheter) may also be used in conjunction with the other methods and devices.

The antimicrobial composition can be delivered as a coating that elutes from a coated elongate member, that is coated onto, or impregnated into, the elongate member (such as 250 µg of chlorhexidine acetate in a layer approximately 2 µm thick along a 17 mm long×1.9 mm diameter elongate member/rod). The elongate member has the added benefit of displacing fluid from within the catheter as it is inserted, transferring the solution to the outer proximal region of the catheter connector (end face and threads).

Antimicrobial compositions from the sealing cover dissolves into the displaced fluid, and thereby disinfects the proximal end of the connector. Furthermore, when the fluid dries, it deposits a coating of chlorhexidine acetate or other appropriate antimicrobial composition on the connector as described above. As an alternative to using the elongate member, chlorhexidine acetate or other antimicrobial composition may be delivered by a coating on a luer tip (such as 250 µg of chlorhexidine acetate in a layer that is approximately 20 µm thick). The luer portion is also coated with an antimicrobial composition in some embodiments (such as 50 µg of chlorhexidine acetate in a layer that is approximately 0.4 µm thick). It is also possible to deliver antimicrobial compositions by way of the connector tip cavity (dry dissolvable amount, applicable for Citrate or others requiring large amounts of antimicrobial composition).

In an example implementation, the invention is directed to a method of delivering an antimicrobial composition to the proximal end of a transdermal catheter, the method comprising: a) providing a transdermal catheter implanted within a patient, the transdermal catheter having a proximal end located outside of the patient and a distal end located at least partially within a blood vessel of the patient, the catheter comprising: i) a hub located at the proximal end of the catheter, ii) exterior threads on the proximal end of the hub, and iii) an interior channel in the hub leading from an opening at the proximal end of the catheter to a lumen in the catheter, wherein at least a portion of the interior channel has a tapered interior surface; b) providing an antimicrobial composition delivery device for insertion into the proximal opening of the catheter, the antimicrobial composition delivery device comprising: i) a tapered member configured for insertion into the catheter hub, the tapered member configured to substantially seal the proximal end of the catheter, ii) an elongate member extending from the tapered member, the elongate member configured for insertion into the catheter hub, iii) an antimicrobial composition positioned on the elongate member, and iv) a retaining ring comprising threads configured to engage the exterior threads on the catheter hub; c) injecting a liquid lock solution into the transdermal catheter such that at least the proximal end of the transdermal catheter is substantially filled with the lock solution; d) applying a clamp across the proximal end of the catheter, the clamp substantially preventing the flow of fluids across the clamped portion of the catheter; and e) after applying the clamp, insertion of the elongate member and tapered member of the antimicrobial delivery device into the hub located at the proximal end of the catheter. The elongate member is retained substantially within the hub of the transdermal catheter; wherein the tapered member of the antimicrobial delivery device sealingly engages the tapered member of the hub of the catheter; and wherein the antimicrobial composition elutes into the lock solution on the proximal end of the clamp.

In certain embodiments, upon insertion of the elongate member into the catheter hub, the antimicrobial composition does not enter the distal end of the catheter or the patient.

In certain embodiments, upon insertion of the elongate member and tapered member into the hub, at least a portion of the lock solution flows backwards out of the hub so as to moisten the threads on the retaining ring and the threads on the hub.

In certain embodiments, upon insertion of the elongate member and tapered member of the antimicrobial delivery device into the hub: the interior of the hub defines a first volume of lock solution, a second volume of lock solution, and a third volume of lock solution; the first and third volumes of lock solution being separated by the second volume of lock solution; and the second volume of lock solution having a constriction such that it has a smaller cross sectional area than the first volume of lock solution or third volume of lock solution.

In certain embodiments, upon insertion of the elongate member and tapered member of the antimicrobial delivery device into the hub: the interior of the catheter defines a first volume of lock solution, a second volume of lock solution, and a third volume of lock solution, the first volume of lock solution having an average diameter greater than the average diameter of the second volume, the second volume of lock solution having an average cross sectional area less than the average cross sectional area of first volume and third volume, and the third volume of lock solution having a cross sectional area substantially equal to the average lumen cross sectional area of the catheter proximal to the clamp. In certain implementations the first volume of lock solution comprises lock solution located in the portion of the interior channel of the hub between the end of the tapered member and the end of the tapered interior surface of the interior channel; wherein the second volume of lock solution lock solution located between the end of the tapered interior surface of the interior channel and the end of the elongate member; and wherein the third volume of lock solution comprises lock solution located within the catheter between the end of the elongate member and the clamp. Optionally the second volume is less than the first volume, and the first volume is less than the third volume. In certain embodiments, upon insertion of the elongate member and tapered member into the hub, antimicrobial concentration in the first volume is initially higher than antimicrobial concentrations in the third volume. In certain embodiments, the antimicrobial concentration in the first volume after 48 hours is at least ten times higher than the antimicrobial concentration in the third volume. In certain embodiments, the amount of antimicrobial in the first and second volumes after 48 hours is at least three times higher than the amount of antimicrobial in the third volume.

The antimicrobial composition forms a precipitate that possesses antimicrobial properties in some implementations; the precipitate is deposited on the interior of the hub.

In some implementations the antimicrobial composition is coated on the elongate member. In some implementations the elongate member is entirely proximal to the clamp. In some implementations the elongate member is contained fully within the hub. Optionally the elongate member has a cross sectional area of at least 25 percent of the cross sectional area of the narrowest point in the channel in the hub.

The elongate member may have (for example) a cross sectional area of at least 50 percent of the cross sectional area of the narrowest point in the channel in the hub, a cross sectional area of at least 75 percent of the cross sectional area of the narrowest point in the channel in the hub, or a cross sectional area less than 90 percent of the cross sectional area of the narrowest point in the channel in the hub.

In some embodiments the transdermal catheter is a hemodialysis catheter having two hubs, and wherein two antimicrobial devices are installed on the two hubs.

Typically the elongate member has a length that is greater than the length of the tapered member. The elongate member may have a cross sectional area less than 50 percent of the average cross sectional area of the tapered member. Optionally the elongate member has a cross sectional area less than 50 percent of the greatest cross sectional area of the tapered member. In some embodiments the elongate member has a cross sectional area less than 50 percent of the smallest cross sectional area of the tapered member. The elongate member may have a volume at least 50 percent of the volume of the tapered member. In certain embodiments the elongate member displaces a volume at least 0.03 mL out of the hub. The tapered member and elongate member can be rigidly affixed to one another and not separable.

The present invention is also directed to a method of coating an antimicrobial composition on the proximal end of a transdermal catheter, the method comprising: a) providing a transdermal catheter implanted within a patient, the transdermal catheter having a proximal end located outside of the patient and a distal end located at least partially within a blood vessel of the patient, the catheter comprising: i) a hub located at the proximal end of the catheter, ii) exterior threads on the proximal end of the hub; iii) an interior channel leading from an opening at the proximal end of the catheter to a lumen in the catheter, wherein at least a portion of the interior channel has a tapered interior surface; b) providing an antimicrobial delivery device for insertion into the proximal opening of the catheter, the device comprising: i) a tapered member configured for insertion into the catheter hub, the tapered member configured to substantially seal the proximal end of the catheter, ii) an elongate member extending from the tapered member, the elongate member configured for insertion into the catheter hub, iii) an antimicrobial composition positioned on the antimicrobial delivery device, and iv) a retaining ring comprising threads configured to engage the exterior threads on the catheter hub; c) injecting a liquid lock solution into the transdermal catheter such that at least the proximal end of the transdermal catheter is substantially filled with the lock solution; d) applying a clamp across the proximal end of the catheter, the clamp substantially preventing the flow of fluids across the clamped portion of the catheter; and e) after applying the clamp, insertion of the elongate member and the tapered member of the antimicrobial delivery device into the hub located at the proximal end of the catheter; wherein upon insertion of the elongate member, the antimicrobial composition forms an antimicrobial precipitate within the lock solution; and wherein the antimicrobial precipitate coats the internal channel of the hub of the catheter. Optionally, upon the antimicrobial precipitate coating the internal channel of the hub, the antimicrobial agent and the antimicrobial precipitate are not delivered into the catheter lumen distal to the clamp or into the patient. Also, the antimicrobial precipitate can be formed through a chemical reaction involving a chlorhexidine ion and a chlorine ion.

The following detailed description presents a description of certain specific embodiments to assist in understanding the claims. However, one may practice the present invention in a multitude of different embodiments as defined and covered by the claims.

In one aspect, the present invention includes an organism barrier at the external end of the catheter, also referred to herein as the proximal end of the catheter. This barrier provides a seal to keep organisms from reaching the end face and luer portions of the connector on a catheter. This can be accomplished in a first embodiment by placing an elastomeric flap or gasket (i.e., silicone, neoprene, polyurethane, etc.) that is positioned at the end of the sealing cover's connector or, alternatively, along the inner wall of the sealing cover's locking-ring. The flap preferably makes a fluid tight seal against the outer wall of the catheter's connector, thereby decreasing the likelihood of microbial incursion and preventing microbial growth. In the alternative, a barrier may be formed by placing foam, either closed cell or open cell, that preferably contains an antimicrobial composition, along the inner wall of the sealing cover's retaining ring and/or at the most proximal location in the sealing cover such that it will abut and seal against the proximal end of the catheter's connector surface (also called the end face).

An embodiment using an antimicrobial composition along the sealing cover's thread region, but not containing an organism barrier, can also be used to reduce the number of organisms that can enter the catheter. This reduction in the number of organisms that can enter the catheter can be accomplished by killing organisms within the thread and end face region.

The sealing cover is optionally designed to transfer antimicrobial composition from the sealing cover to the catheter threads. This is accomplished, for example, by displacing fluid from the catheter into the thread region of the connector. In certain embodiments an elongate member and luer, when entering the catheter, displace the catheter's fluid, causing the fluid to flow out into the thread region between the connector and the sealing cover. Antimicrobial composition dissolves in the fluid, causing the fluid to become saturated with antimicrobial composition. The antimicrobial fluid produces an effective antiseptic region, killing organisms on the connector. Furthermore, as the fluid dries, antimicrobial precipitates from the fluid and is deposited onto the catheter threads and end face. This process is repeated every time a new sealing cover is placed onto the catheter, thus replenishing the antimicrobial composition on the catheter's proximal region with each new sealing cover.

In a further aspect, the invention is directed to adding of an antimicrobial composition along a luer connector. This can be accomplished, for example, by coating a male luer connector with various antimicrobial compositions.

In an additional aspect, the invention is directed to delivery of an antimicrobial composition inside the catheter. The antimicrobial can be delivered as a coating that elutes from a coated elongate member that is coated on (or impregnated into) an elongate member. The elongate member has the added benefit of displacing fluid from within the catheter as it is inserted, thereby transferring the fluid to the outer proximal region of the catheter connector (end face and threads). Antimicrobial composition from the sealing cover dissolves into the displaced fluid, thereby disinfecting the proximal end of the connector.

Furthermore, when the fluid dries, it deposits a coating of chlorhexidine acetate or other appropriate antimicrobial composition onto the connector as described above. As an alternative to using the elongate member, the chlorhexidine acetate or other antimicrobial composition may be delivered by a coating on a luer tip (such as 250 μg of chlorhexidine acetate in a layer that is approximately 20 μm thick). A minimum of 10 μg of chlorhexidine acetate on the elongate member is effective for many organisms in some implementations. A desirable minimum of greater than 100 μg is effective for most organisms, and a further desired minimum of 250 μg is highly effective against all of the major target organisms.

Types of antimicrobial compositions can include, without limitation, chlorhexidine base, chlorhexidine acetate, chlorhexidine gluconate, EDTA, iodine, silver sulfadiazine, or Taurolidine; or combinations thereof. Other antimicrobial compositions may also be used.

Typically these methods are also used in conjunction with confinement of the antimicrobial in the catheter, such as by relying on a catheter clamp to confine the antimicrobial composition in a portion of the proximal end of the catheter (that portion of the catheter outside of a patient and in particular that portion nearest the connector on the catheter by which fluids enter and leave the catheter). Extension tube clamps are typically part of each hemodialysis catheter and are currently used to confine lock solutions that are used to help ensure catheter patency. Using the existing clamp methodology, the risk of air embolus and lock solution entering the patient is very small and consistent with the current state of the art for conducting hemodialysis procedures. In other medical devices, such as catheters that do not possess catheter clamps, a swellable sealing cover tip or other confinement technique, such as those described in United States patent application publication number US 2010/0106103, may be used.

Organism mechanical removal can also be utilized. In this regard, a portion of the elongate member can scrap the catheter wall upon removal, such as by having ribs incorporated into the elongate member. In some implementations, after placing the elongate member into the catheter, anisotropic swelling moves ribs (or other projections) against the interior wall of the catheter, which provides a tighter fit against the wall after swelling and further promotes mechanical removal of the organisms when the elongate member is removed from the catheter along with the rest of the sealing cap. Also, in some implementations the tip of the elongate member swells (or other portions such as ribs to swell), or swelling occurs along the length of the elongate member. Generally the elongate member's unswollen diameter is smaller than the catheter lumen when the elongate member is being inserted, but swells to conform to the inner shape (or larger) of the catheter lumen to enhance the mechanical removal of the organisms during removal. Various polyurethanes or other material may be used to produce suitable anisotropic swelling and mechanical stability; more specifically, Lubrizol 1065D is suitable for a non-swelling elongate member and TG-500 is suitable for an anisotropic swelling (or isotropic swelling) tip which may be bonded with each other using heat bonding or other suitable methods.

An embodiment of the invention, herein referred to as a "sealing cover", prevents the migration of infectious organisms into the body by providing an antimicrobial and/or physical barrier preventing movement of infectious organisms in to the catheter, as well as preventing reproduction of infectious organisms within the proximal end of the catheter.

The sealing cover optionally contains an elongate member that can be inserted into a medical device, such as a catheter or a drainage tube. For the sake of simplicity, the term "catheter" is used for all medical devices in which the present invention can be inserted and used to control, prevent, and eliminate infectious organisms. The sealing cover may be removed from the catheter to allow the catheter to be used in a dialysis procedure or other procedure. After the procedure is complete, a new sealing cover may be used to seal and protect the catheter. The removal of one sealing cover and the replacement with a new sealing cover may be repeated an indefinite number of times. With each new sealing cover, the antimicrobial composition inside and outside of the catheter is reestablished. Another aspect is that antimicrobial composition is transferred from the sealing cover to the catheter with each use.

In the case of using the sealing cover with dialysis catheters, the present invention is generally designed to be replaced regularly after each dialysis session, approximately three times per week. This replenishes the antimicrobial composition with each replacement, resulting in a consistent and high concentration of antimicrobial composition present within and upon the catheter on an ongoing basis resulting in decreased risk of infection. However, the confinement method, such as clamps, as used in conjunction with the invention, prevents a significant amount of antimicrobial composition from leaking into the bloodstream on a regular basis, which also maintains a higher concentration of antimicrobial composition in the proximal end of the catheter, where a significant danger of microbe infiltration exists.

In addition, separation between the antimicrobial composition and blood can result in lower infection rate, fewer side effects, and less risk of developing resistant bacteria because a non-antibiotic antimicrobial is used. In certain embodiments, the present invention creates a physical barrier between the blood and the antimicrobial composition. The barrier greatly reduces the exchange of antimicrobial composition with blood circulating in the body, resulting in fewer side effects from the antimicrobial composition. This can result in a more consistent level of antimicrobial composition along the length of the catheter adjacent to the sealing cover. Additionally, the barrier reduces the amount of antimicrobial composition entering the bloodstream, thus reducing the risk of an adverse reaction to the composition or developing organisms resistant to the antimicrobial composition.

In comparison, it is well-known that liquid locking compositions can and do routinely migrate into the bloodstream, and the blood can migrate into the catheter, thus reducing the effectiveness of the antimicrobial composition, increasing the possibility of bacteria entering the bloodstream and increasing the rate of thrombosis in the catheter. The act of flushing the catheter lumen with a fluid composition into the lumen will result in the removal of blood from the lumen and thus reduce the risk of thrombosis. If the liquid composition is an anti-thrombotic lock, such as heparinized saline or saline with 4% sodium citrate, the risk of thrombosis is further reduced. The use of a confinement means, as described in the present invention as a swellable elongate member tip, swellable elongate member, or catheter clamp, prevents the blood from reentering the lumen and results in a lower risk of thrombosis in the lumen.

A further aspect of the invention relates to protecting the sealing covers from contamination prior to use and during handling in order to keep the elongate member and luer sterile prior to insertion into the catheter. A package that covers the elongate member and luer may be used. A standard package, which protects one luer and elongate member, is suitable for keeping one elongate member and luer sterile. A novel package is hereafter described which improves handling while maintaining sterility protection, and facilitates low-cost injection molding.

The packaging container holds two sealing covers, where the two sealing covers are held 180 degrees opposed in an axially offset manner, typically with at least a portion of the two elongate members axially overlapping one another, with a physical barrier between the two sealing covers. The packaging container functions as a shield to protect the sealing cover, and also to maintain sterility of the sealing cover as well as to prevent loss of the antimicrobial composition located on the portions of the sealing cover that will be inserted into the catheter.

The packaging container may have threads to provide a means for removably attaching the sealing covers to the packaging body. This configuration allows the user to hold one piece rather than two, thus easing handling and decreasing the risk of dropping the sealing covers. The barrier between the two sealing covers ensures that, when one sealing cover is removed from the packaging container, that the other sealing cover remains sterile. The sealing covers, secured within the packaging, may be contained in a pouch using a suitable material, such as a metal film with a polymer laminate to facilitate heat sealing. The metal layer is useful to minimize adverse effects of humidity. The device, inside the pouch, may be sterilized using gamma radiation or other suitable sterilization method. Gamma radiation has the advantage of effectively sterilizing the product while it is contained within moisture-proof packaging.

Referring now to the figures, example implementations of the invention are shown. FIG. 1A shows an exploded view of a packaging container system 210 that includes an arterial sealing cover 220, a venous sealing cover 320, and a packaging container 250. The packaging container system 210 contains two sealing covers within the same packaging container 250. Colors of the sealing covers are typically chosen to match the standard colors used in hemodialysis: red for the arterial sealing cover 220 and blue for the venous sealing cover 320. Typically the arterial sealing cover 220 and venous sealing cover 320 are identical other than color.

Packaging container 250 provides for easier handling and storage of the sealing covers 220 and 320 because there are relatively few parts to handle and hold. The packaging container system 210 is optionally shipped and stored within a heat-sealed foil-pouch (not shown) and gamma sterilized, although other packing and sterilization techniques can be used. The foil-pouch is generally opened at the clinic immediately before use of the sealing covers. Sealing cover threads 141 removably engage packaging container threads 159 to allow easy removal of the sealing covers 220, 320 from the packaging container 250. The sealing cover 220 also shows a central protrusion 131 comprising a further elongate member 133 extending beyond the central protrusion 131. A flattened side 157 of the packaging container 250 creates a convenient feature for gripping the packaging container 250 as the sealing covers 220, 320 are removed. In addition, the flattened side 157 of packaging container 250 disrupts the rotational symmetry of the packaging container 250, thus making the packaging container system 210 resistant to rolling onto the floor or being dropped.

Figure 1B:
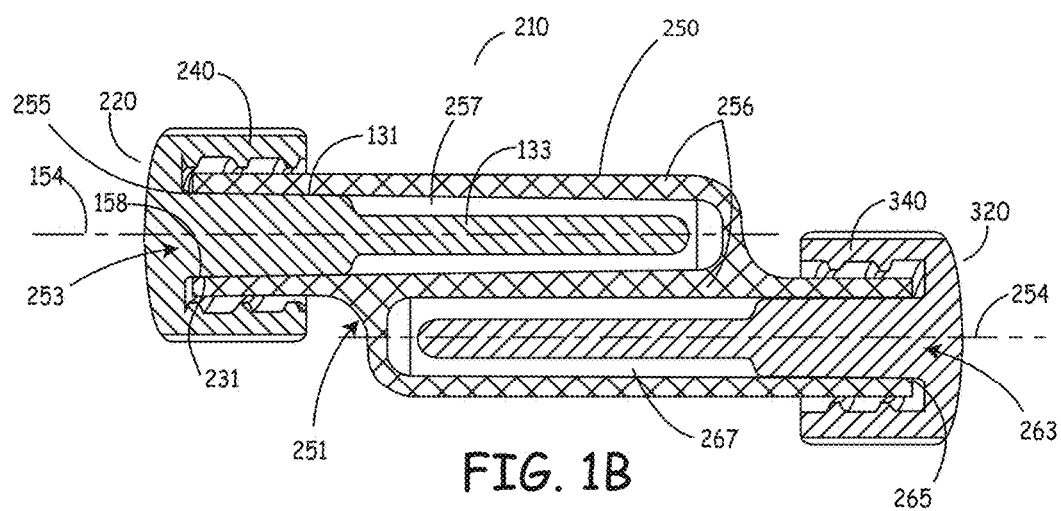
FIG. 1B is a side cross section view of two sealing covers with elongate members inserted into a packaging container made in accordance with an implementation of the invention.

FIG. 1B shows a cross section of a packaging container system 210 with an arterial sealing cover 220 and a venous sealing cover 320, each inserted into a packaging container 250, identical to the packaging container system 210 but with both sealing covers 220 and 320 installed on the packaging container 250. The packaging container 250 is designed to keep the sealing covers 220, 320 axially offset as shown by the arterial sealing cover axis 154 and the 20 venous sealing cover axis 254. The offset axis is advantageous over a coaxial design because it decreases the length of the system 210, allowing it to fit into a shorter pouch and making it easier to handle. The container includes a body 251 with a first end 255, the first end 255 having a first opening 253 leading to a first volume 257 within the body 251; and a second end 265, the second end 265 having a second opening 263 leading to a second volume 267 within the body 251; the first and second openings 253, 263 configured to each hold one of the two antimicrobial covers. In addition, the sealing covers 220, 320 are 180 degrees opposed from each other, thus making the retaining rings 240, 340 physically separated from one another. This makes the retaining rings 240, 340 easier to grasp because the arterial retaining ring 240 does not physically 25 block finger access to the venous retaining ring 340, and vice versa.

The packaging container 250 provides protection to the sealing covers 220, 320 and further promotes sterility prior to use because each of the sealing covers 220, 320 are separated by a wall 256. In an example embodiment, the most proximal portion 231 of a central protrusion 131 on sealing cover 220 contacts the receiving edge 158 of the packaging container 250. The central protrusion 131 functions as a protrusion for subsequently engaging the proximal end of a catheter to seal the proximal end of the catheter. In the embodiment shown in FIG. 1B, the central protrusion 131 includes a further elongate member 133 extending beyond the central protrusion 131. In example embodiments most of the central protrusion 131 does not contact the wall 256, and thereby minimizes the risk of removing antimicrobial coating on the central protrusion 131. Typically the elongate member 133 also does not contact the wall 256 so as to minimize the risk of removing the antimicrobial coating in the event that the elongate member 133 is coated with an antimicrobial composition.

Figure 2A:
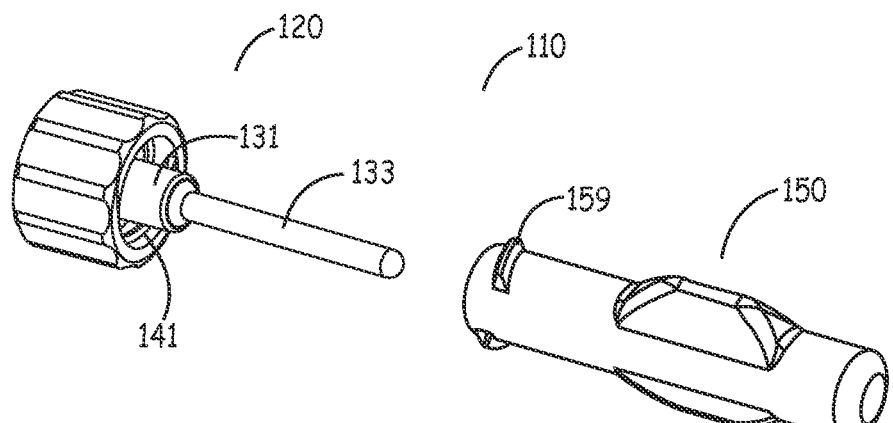
FIG. 2A is a perspective view of a sealing cover with an elongate member and a packaging container made in accordance with an implementation of the invention. The sealing cover is shown with the protrusion and elongate member withdrawn from the packaging container.

FIG. 2A shows a perspective view of a mono packaging container system 110 with a sealing cover 120, and a packaging container 150. The packaging container 150 allows for retention of one sealing cover within the housing of the packaging container 150. The mono packaging container system 110 can be packaged within a heat-sealed foil-pouch (not shown) and gamma sterilized. The foil-pouch is typically opened at the clinic immediately before use of the sealing cover 120. The sealing cover threads 141 removably engage the packaging container threads 159 to allow easy removal of the sealing cover 120 from the mono packaging container 150.

Figure 2B:
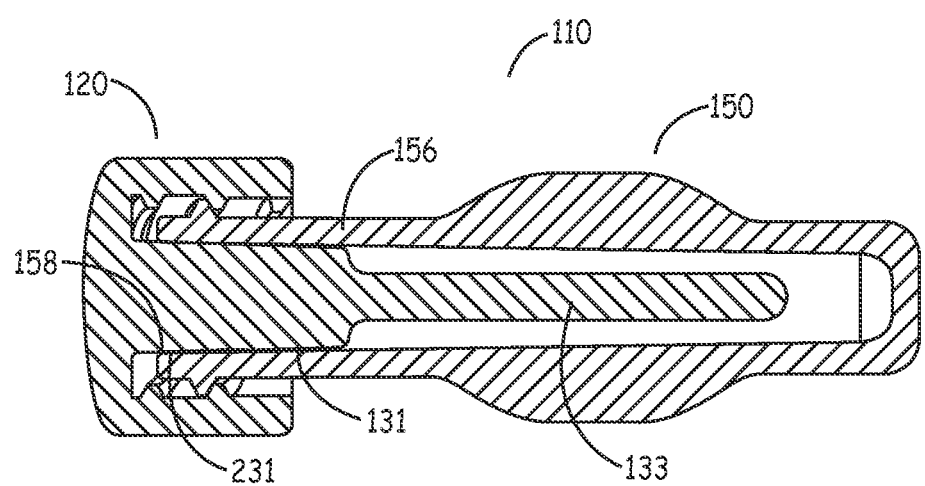
FIG. 2B is a side cross section view of a sealing cover with a protrusion and elongate member inserted into a packaging container made in accordance with an implementation of the invention.

FIG. 2B shows a cross sectional view of the mono packaging container system 110 of FIG. 2A with a sealing cover 120 inserted into a mono packaging container 150. The sealing cover 120 is inserted into the mono packaging container 150. The mono packaging container 150 provides protection to the sealing cover 120 and further ensures that sterility is maintained prior to use. This is accomplished by enclosing the sealing cover 120 by a wall 156. In an example embodiment the most proximal portion 231 of the central protrusion 131 contacts the receiving edge 158 of the mono packaging container 150. In this example embodiment the rest of the central protrotrusion 131 does not contact the wall 156, and thereby minimizes the risk of removing antimicrobial coating on the central protrusion 131. The elongate member 133 also preferably does not contact the wall 156 in order to minimize the risk of removing the antimicrobial coating.

Figure 3A:
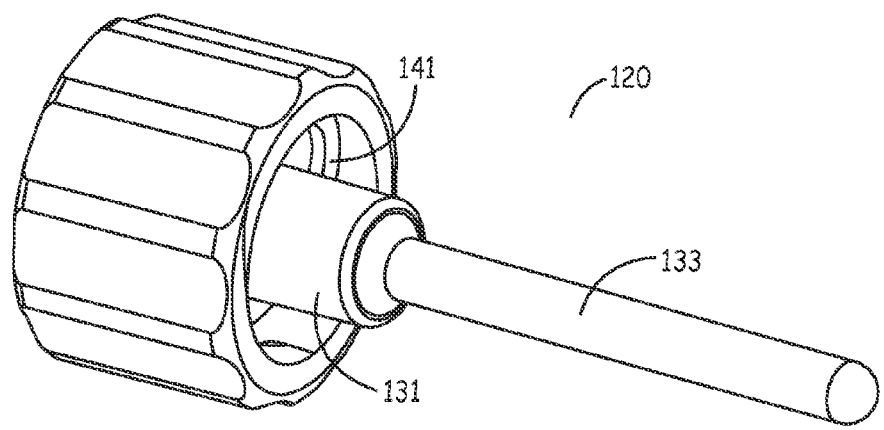
FIG. 3A is a perspective view of a sealing cover made in accordance with an implementation of the invention.

FIG. 3A shows a sealing cover 120 made in accordance with an example implementation of the invention. The sealing cover 120 can be, in certain example implementations, injected molded as a single unit out of a thermoplastic polymer resin to allow high volume production at low manufacturing costs. The sealing cover 120 includes a central protrusion 131 formed as a male luer connector configured to engage a female luer connection at the proximal end of a transdermal catheter. The central protrusion 131 formed as a male luer connector in the depicted embodiment includes a further elongate member 133. The elongate member 133 optionally functions to deliver antimicrobial compositions into the interior of the proximal end of transdermal catheters.

In addition, the elongate member 133 provides a volume that aids in displacing fluids within the proximal end of transdermal catheters, including displacing fluids such that they exit from the proximal end of the transdermal catheter so as to deliver antimicrobial compositions to the proximal end of the transdermal catheter (such as to the end of the catheter hub and the threads on the catheter hub. This displacement of fluid, combined with the delivery of an antimicrobial composition into the catheter, results in a flow of antimicrobial composition containing fluid out through the proximal end of the transdermal catheter. In the alternative, or in addition, the displacement of fluids from the proximal end of the transdermal catheter can result in moistening antimicrobial compositions that are coated on the central protrusion 131 formed as a male luer connector, as well as on the sealing cover threads 141 and on the interior of the sealing cover 120. This moistening of the antimicrobial composition can bring the antimicrobial composition into solution, thereby killing microbes near the proximal end of the catheter—both within the catheter and, in specific embodiments, on the outside of the catheter.

In this manner, antimicrobial compositions are delivered to locations along the exit path for the displaced fluid: along the luer connection, at the end of the transdermal catheter, and at threads on both the sealing cover 120 and on the external threads on the proximal end of the catheter. Thus, multiple processes can combine to reduce the population of microbes at the proximal end of the catheter, thereby preventing or limiting their migration into the interior of the catheter, from where they could otherwise subsequently migrate into a patient's bloodstream.

The elongate member 133 is generally formed of a polymeric material that allows it to be bent without breaking. Polymers with a minimum elongation at break of 100% are preferred. In addition, the polymer will typically allow a solvent (which is used in the antimicrobial composition coating process) to wet the surface evenly until the solvent evaporates, and an antimicrobial composition will typically adhere well to the surface of the elongate member 133 such that the coating does not flake or fall off during handling. Various polymer materials may be used that meet these requirements, such as polyester, nylon, polyetherimide, polypropylene, polyvinyl chloride or other similar materials. Alternatively, the elongate member 133 may be manufactured using a dissolvable material that is impregnated with an antimicrobial composition, such that the antimicrobial is released into the solution when the elongate member 133 dissolves.

Portions of the sealing cover 120 are typically coated and/or impregnated with an antimicrobial composition. In one embodiment, the antimicrobial composition is applied as a coating, with different amounts optionally applied to the elongate member 133, the central protrusion 131, and the sealing cover threads 141. The antimicrobial composition can also be incorporated within the bulk polymer material, but coating the surface is preferred because surface coatings can generally be released into solution more rapidly than bulk agents; additionally surface coatings tend to require less overall antimicrobial composition than bulk agents because the antimicrobial composition on the surface is more readily dissolved. In some implementations a combination of surface coatings and incorporation into bulk polymer materials is used.

Suitable methods of coating the sealing cover 120 are spraying and dipping, with spray coating being desirable because the amount of antimicrobial composition applied to each region (elongate member 133, central protrusion 131, and sealing cover threads 141) can more easily be adjusted without affecting the amount located on other regions.

Silicone, fluropolymers or other lubricious coatings may also be applied to the central protrusion 131 to reduce the amount of torque required to remove the sealing cover from the catheter hub.

Figure 3B:
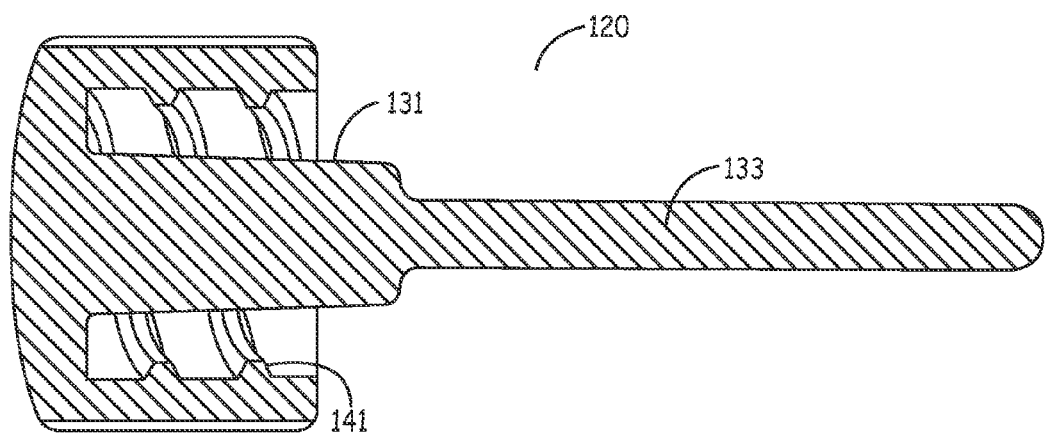
FIG. 3B is a side cross section view of the sealing cover of FIG. 3A made in accordance with an implementation of the invention.

FIG. 3B shows a cross section of a sealing cover 120 made in accordance with an embodiment of the invention. The length and diameter of the elongate member 133 is sized to fit into the proximal end of a catheter, in particular into the hub of a catheter. In the embodiment described herein, the catheter is a hemodialysis catheter. The central protrusion 131 and the sealing cover threads 141 can be manufactured in accordance with the International Organization for Standardization standard ISO 594-2:1998(E) to be compatible with all hemodialysis catheters which are made according to the standard. In certain embodiments the cover threads 141 are coated with an antimicrobial composition.

Figure 4A:
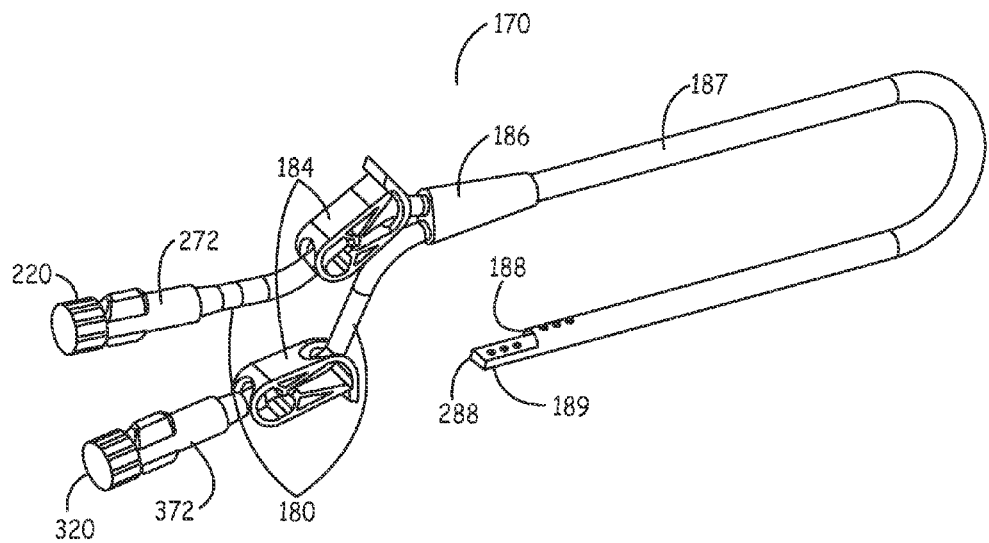
FIG. 4A is a perspective view of two sealing covers made in accordance with an implementation of the invention. The two sealing covers are shown mounted onto the proximal end of a catheter.

FIG. 4A depicts an example hemodialysis catheter 170 for use in conjunction with an embodiment of invention, and is shown with an arterial sealing cover 220 in the arterial hub 272, and a venous sealing cover 320 in the venous hub 372. When used with a hemodialysis patient, the two-lumen tube 187 is partially tunneled below the patient's skin, from the upper chest to the jugular vein. The two-lumen tube 187 enters the jugular vein and continues until the catheter tip 189 is in the region of the right atrium of the heart. The arterial lumen 188 runs inside the catheter 170 from the arterial hub 272 until exiting at the catheter tip 189. The venous lumen 288 similarly runs inside the catheter 170 until it exits near the catheter tip 189. If bacteria or fungus are in either or both lumens 188, 288, these infection-causing organisms may enter the bloodstream and result in a systemic bloodstream infection, and therefore prevention of the entry and growth of microorganisms into the catheter 170 is important.

The catheter contains a junction 186 where the extension tubes 180 transition from two tubes with two lumens into one tube with two lumens; the two lumens 188, 288 run from hubs 272, 372 to catheter tip 189 without fluidly connecting with the other lumen. The arterial hub 272 is attached to the proximal end of one extension tube 180, and the venous hub 372 is attached to the proximal end of the other extension tube 180. In the depicted embodiment, a clamp 184 is positioned on each of the extension tubes 180, allowing the flow in the lumen to be blocked or opened. In practice, the clamps 184 are closed except during a dialysis session or other transferring of fluids within the catheter 170. The clamps 184 are typically repositioned each time they are opened in order to minimize the risk of damaging the extension tube 180 through multiple clamping in the same location. The clamps 184 are generally closed prior to insertion of either sealing cover 220, 320. In this manner, the sealing covers 220, 320 do not have any portion that project deeply into the catheter. Instead, in an example embodiment, the design is such that the sealing covers primarily project into the hubs 272, 372 with elongate member 133 (see FIG. 3B, for example), being contained in the proximal end of the catheter, often just in the hub, such as so they may be inserted while the clamp is closed. This design also provides for the forcing of fluid with the proximal end of the catheter out the end of the catheter upon insertion of the elongate member into the catheter hub. Thus, the design as shown actually promotes the flow of fluid out the proximal end of the hub, rather than deeper into the catheter.

Figure 4B:
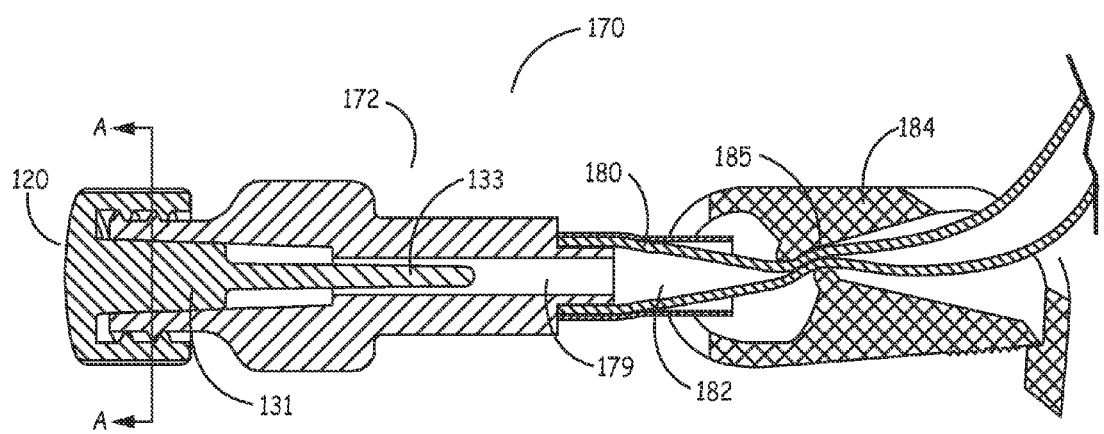
FIG. 4B is a side cross section view of a sealing cover made in accordance with an implementation of the invention, the sealing cover mounted onto a catheter.

In reference to FIG. 4B, a cross section of the proximal end of a catheter and sealing cap are shown. Clamp 184 is shown located in close proximity to the hub 172. The clamp 184, when closed, creates a pinch point 185 which blocks the fluid flow in the lumen, creating a proximal region in the catheter lumen on the proximal side of the clamp, and a distal region in the catheter lumen distal from the clamp. Preferably the elongate member 133 is short enough to ensure that the clamp 184 does not clamp onto the elongate member 133. Thus, the elongate member typically does not extend beyond the hub 172. The elongate member 133 should preferably be stiff enough to allow for insertion into the hub 172 without requiring sheaths, tubes or other insertion aids.

In addition, the elongate member 133 must possess a small enough diameter to ensure that it can physically fit within the hub lumen 179. In embodiments where the elongate member 133 is long enough to enter extension tube 180 extending from the hub 172, the diameter of the extension tube 180 must also accommodate the elongate member.

The surface area of the elongate member 133 should be large enough to allow for the desired amount of antimicrobial composition to be coated on the surface using spraying or dipping operations (or other application methods, including incorporation directly into the elongate member). The surface area is generally sized to produce an acceptable dissolution rate such that the antimicrobial composition enters the lock solution at an acceptable rate and dosage. It is desirable for the antimicrobial composition to reach an effective level within an hour of the sealing cover 120 being inserted into the catheter 170.

If the elongate member extends into the pinch point 185 of the clamp 184, it can potentially cause damage or leaking of the lock solution present within the catheter. Therefore the length of the elongate member 133 should be sufficiently short to ensure that it does not reach the pinch point 185 of the clamp 184. Suitable diameters for the elongate member 133 include 1.0 mm to 2.0 mm; and 1.7 mm to 1.9 mm. A suitable length includes less than 20 mm for the elongate member 133, alternatively less than 10 mm, less than 30 mm, or less than 40 mm. A particularly desirable length is 17 mm to 19 mm, but can vary for use with various catheters. Typically the elongate member 133 is longer than central protrusion 131. For example, the elongate member can be from 1 to 10 times the length of the central protrusion 131. In some implementations the elongate member can be from 1 to 5 times the length of the central protrusion 131, in certain embodiments the elongate member is from 1 to 2.5 times the length of the central protrusion 131. It is also possible to have the elongate member 133 be shorter than the central protrusion 131. Generally the elongate member 133 is significantly thinner than the central protrusion 131, such as less than half the diameter of the widest diameter of the central protrusion 131.

Figure 4C:
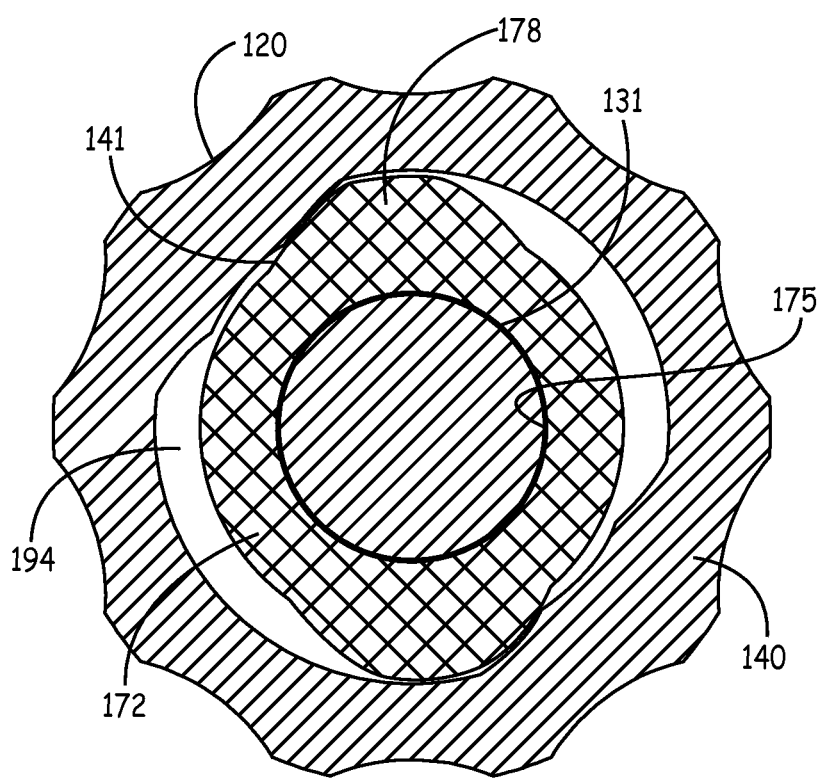
FIG. 4C is an end cross section view of a sealing cover made in accordance with an implementation of the invention and inserted into a catheter.

In reference now to FIG. 4C, an embodiment is depicted showing the end section view A-A as indicated in FIG. 4B. The sealing cover 120 is shown fully inserted into the catheter hub 172. When fully inserted, the central protrusion 131, formed as a male luer, contacts the female luer 175 to create a fluid tight seal. Threads 141 of the sealing cover 120 engage the catheter threads 178 to retain the sealing cover 120 on the hub 172. However, even after the sealing cover 120 is fully inserted into the hub 172, a void 194 is often present between the retaining ring 140 on the sealing cover 120 and the hub 172. This void 194 can be a pathway for pathogenic organisms to travel along, thus allowing contamination of the hub surfaces with pathogenic organisms in the region between the retaining ring 140 and the hub 172.

In order to reduce the incidence of catheter-related bloodstream infections, it is desirable to reduce or eliminate the number of pathogenic organisms in this region.

Figure 5A:
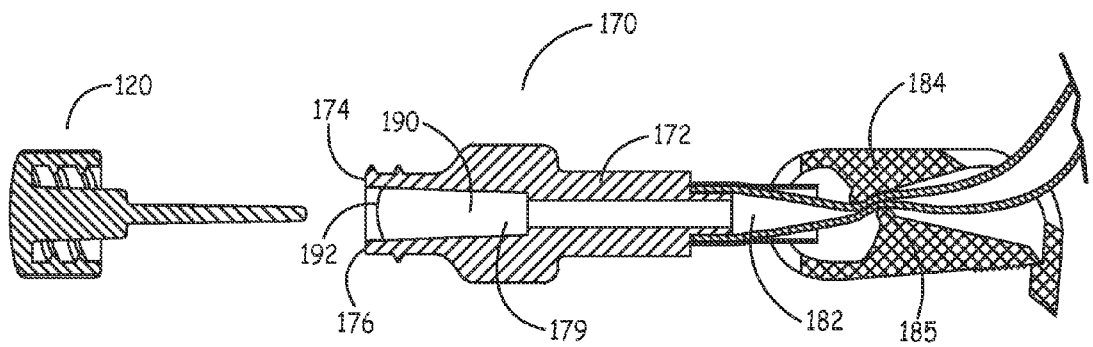
FIG. 5A is a side cross section view of a sealing cover made in accordance with an implementation of the invention, prior to the sealing cover inserted into a catheter.
Figure 5B:
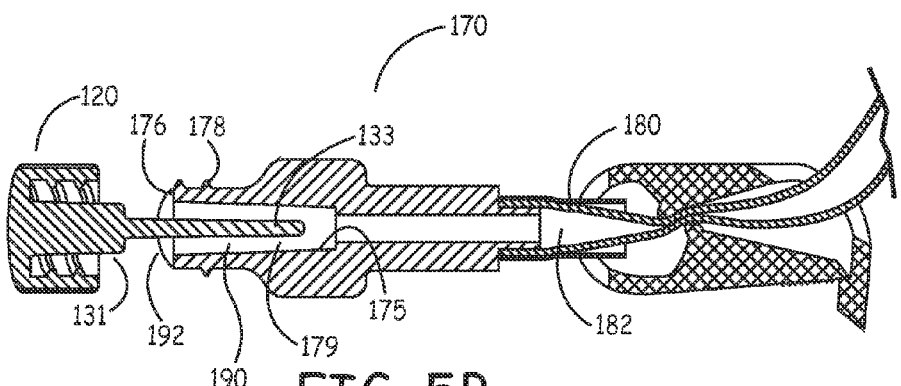
FIG. 5B is a side cross section view of a sealing cover made in accordance with an implementation of the invention, with the sealing cover shown being mounted onto the catheter and an elongate member being inserted into the catheter.
Figure 5C:
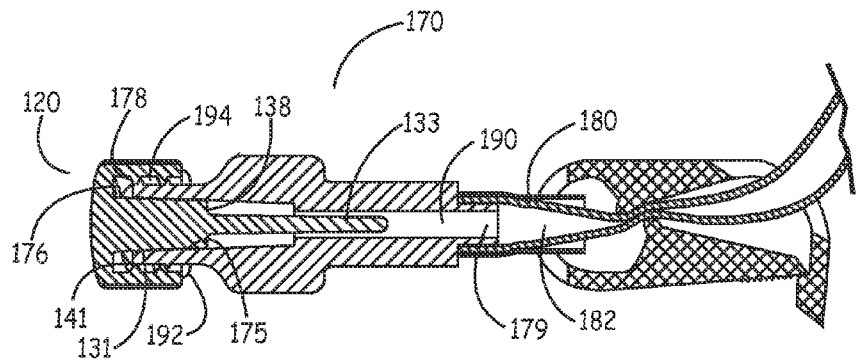
FIG. 5C is a side cross section view of a sealing cover made in accordance with an implementation of the invention, with the sealing cover shown mounted onto the catheter and an elongate member inserted into the catheter.

Referring now to FIG. 5A to 5C, various stages of installation of sealing cover 120 are shown, wherein the insertion of the sealing cover (with an elongate member) results in the flow of an anti-microbial containing liquid out the end of the catheter hub to kill microorganisms that would otherwise potentially intrude into the hub and then the catheter lumen. In FIG. 5A, the sealing cover 120 is shown immediately prior to being inserted into the hub 172 of a catheter 170. Within the hub lumen 179 is a liquid lock solution 190, the most proximal portion of which forms a meniscus 192. The lock solution for hemodialysis catheters is most often heparinized saline (100 IU/ml to 5000 IU/ml of heparin), sodium citrate solution (typically 4% sodium citrate), or saline. Patient care technicians and nurses are trained to keep the meniscus 192 at the proximal end 174 of the hub 172. However, it is not unusual for the meniscus to fall several millimeters within the hub lumen 179. The antimicrobial composition must produce the desired effect in any of the standard lock solutions. In practice, the clamp 184 remains closed (producing a pinch point 185) unless fluids are being transferred through the catheter 170.

In reference to FIG. 5B, the elongate member 133 is shown partially inserted into the hub lumen 179. The elongate member 133 displaces lock solution 190, which results in the meniscus 192 being pushed out of the lumen 179 and onto the end face 176 of the hub 170. Eventually, as the sealing cover 120 continues to be inserted, the meniscus 192 (and lock solution 190) will travel over the catheter threads 178, bringing antimicrobial to those threads.

Next, referring to FIG. 5C, the sealing cover 120 is shown fully inserted into the catheter 170. In this embodiment, the meniscus 192 travels beyond the void 194, completely filling the void 194 with lock solution. The lock solution causes the antimicrobial composition to dissolve, resulting in a transfer of antimicrobial composition from one or more of the coated parts (the elongate member 133, the central protrusion (male luer) 131, and sealing cover threads 141) into the solution. In addition, insertion of the elongate member into the lock solution further causes a transfer of antimicrobial composition to the previously uncoated parts such as the wall defining the inner hub lumen 179 and extension lumen 182, the female luer 175, the end face 176, and the catheter threads 178. Within several hours the solution within the void 194 may dry, but a coating of an antimicrobial composition remains.

In this manner a coating of an antimicrobial composition becomes transferred to the catheter threads 178 and the end face 176, resulting in an enhanced ability to kill any organisms on the catheter threads 178 and the end face 176, even if the organisms contaminate the surfaces after the solution dries. In practice, the void is often times infiltrated with sweat that contains organisms. In this scenario the dried antimicrobial composition becomes hydrated by the sweat, killing organisms that may be present in the sweat. Furthermore, the catheter threads 178 and the end face 176 become replenished with additional antimicrobial composition every time a new sealing cover 120 is inserted. In current practice, a new sealing cover is used after every dialysis session. The ability of the sealing cover 120 to replenish the antimicrobial composition on a catheter 170, into a targeted location with a high risk of serving as a microorganism source, overcomes a significant shortcoming of antimicrobial coated catheters in which the antimicrobial composition wears off with use or is only applied to the interior of the catheter. A desirable amount of antimicrobial composition on the catheter threads 178 and sealing cover threads 141 is 20 µg to 2 mg, alternatively 200 µg to 1.5 mg, and desirably 500 µg to 1.2 mg of chlorhexidine acetate. However, it will be understood that different levels can also be achieved with success.

Typically the central protrusion 131 makes contact with the female luer 175 to create a fluid tight seal. These parts are typically manufactured in accordance with the International Organization for Standardization standard ISO 594-2:1998(E) in order to ensure proper sealing and intermateability. However, the junction between the male luer forming the central protrusion 131 and the female luer 175 is not fluid tight along the entire length of the interface. Some manufacturers of medical device hubs intentionally manufacture their female luers such that the male luer contacts the female luer near the male luer end face. This is done in order to reduce the risk of the splitting the hub. However, the unintended consequence is that proximal end of the luer interface allows for the potential infiltration of organisms.

Under prior practice, once the organisms are present, they may be pushed further into hub lumen 179 by current sealing covers (or other devices) the next time a sealing cover (or other device) is inserted. Once the organisms are within the hub lumen (distal to the male luer) they can multiply, resulting in planktonic and sessile organisms, and eventually a biofilm. This problem can be countered by placing an antimicrobial composition along the central protrusion 131. The antimicrobial composition kills organisms that may be or become present along the female luer 175 before the organisms have a chance to be pushed into the hub lumen 179 or further multiply. Even with these protective measures, there is still a possibility that some organisms can make it beyond the female luer 175. To overcome that potential shortcoming, antimicrobial composition may also be present on the elongate member 133, which dissolves or elutes into the lock solution 190, to kill organisms in the hub lumen.

The minimum amount of antimicrobial composition on the elongate member 133 is the amount required to obtain an acceptable reduction (also referred to as kill) of infection causing organisms. The volume of solution that the antimicrobial composition dissolves into is important to understand because the more solution that is present, the more dilute the antimicrobial composition can become. The confined volume of lock solution 190 within the lumen is defined by the location of the meniscus 192, the geometry of the hub lumen 179, the geometry of the extension lumen 182, and the location of the pinch point 185. Since each of these items may vary, there is a considerable range of confined fluid volumes that is possible. After accounting for the design variations of existing hemodialysis catheters, it is evident that an example embodiment needs to produce a therapeutic concentration of antimicrobial composition within a 0.7 ml volume. In one embodiment, the amount of chlorhexidine acetate on the elongate member 133 is 10 µg to 5 mg. In an alternative embodiment, the amount of chlorhexidine acetate is 100 µg to 2 gm. In yet another embodiment, the elongate member contains 250 µg to 550 µg of chlorhexidine acetate.

The desired maximum amount of antimicrobial composition that is placed on each of the sealing cover's surfaces was developed by first reviewing how much antimicrobial is safe for the patient and then comparing that to how much antimicrobial composition the patient can potentially be exposed to by each of the sealing cover's 120 surfaces that contain antimicrobial composition (elongate member 133, central protrusion 131, and sealing cover threads 141). The amount of antimicrobial that is safe for the patient was determined by reviewing published information on levels (especially bloodstream levels) that are generally regarded as safe for patients.

Testing was conducted in order to derive how much antimicrobial composition the patient can potentially be exposed to from sealing cover 120. The testing was designed to determine the transfer efficiency of antimicrobial composition from each applicable component (elongate member 133, central protrusion 131, and sealing cover threads 141) to the bloodstream. In order to determine the potential bloodstream level, consideration was given for potential patient exposure that could occur under a variety of conditions, including unusual use or misuse (such as injecting the lock solution into the patient's bloodstream instead of aspirating the solution). The potential patient exposure was determined for each component individually and for the entire sealing cover 120.

These embodiments can produce broad spectrum kill of the target organisms, yet result in a low enough dose of chlorhexidine acetate that, even if all of the lock solution containing chlorhexidine acetate is injected directly into the bloodstream, it will result in a bloodstream level that remains at safe levels. Thus, the present invention is characterized by relatively high concentrations of antimicrobial compositions in the relatively low fluid volumes, but the quantity of actual antimicrobial used is relatively small. Also, the antimicrobial is generally able to be kept from meaningfully being added to the patient's bloodstream because the antimicrobial is generally contained to the proximal (outside of the body) portion of the catheter, and because relatively small quantities of antimicrobial materials are even used.

Furthermore, it will be understood that in typical embodiments a certain percent of the antimicrobial doesn't even get delivered and retained within the catheter, but rather is delivered to the exterior proximal end of the catheter, such as the end of the hub and threads on the exterior of the hub. This positioning of the antimicrobial in these locations results in potentially higher exclusion of microbial organisms, while also avoiding adding antimicrobial compositions to the patient's bloodstream. In some example implementations up to 50 percent of the antimicrobial is delivered to the outside surfaces of the proximal end of the catheter; in other implementations up to 25 percent of the antimicrobial composition is delivered to the outside surfaces of the proximal end of the catheter; and in yet other implementations up to 10 percent of the antimicrobial composition is delivered to the outside surfaces of the proximal end of the catheter.

In an embodiment of the invention the antimicrobial composition is chosen for its ability to form fine antimicrobial particles within the lock solution through a chemical reaction known as precipitation. The preferred antimicrobial composition forms precipitate within the most common lock solutions such as heparin and saline. The preferred antimicrobial composition creates a precipitate that settles on the catheter wall at the proximal end of the catheter, resulting in an effective antimicrobial coated catheter. A preferred antimicrobial composition is chlorhexidine acetate. Other antimicrobial compositions may also be chosen for their ability to precipitate, such as the other chlorhexidine salts.

In such embodiments, a substantial amount of chlorhexidine precipitate remains on the wall of the catheter, even after flushing the lock solution from the catheter and further rinsing with a saline flush, thus it has been demonstrated that the invention imparts antimicrobial properties to the catheter even after the antimicrobial delivery device is removed. In addition, in certain embodiments the amount of antimicrobial composition on the catheter wall increases with repeated use of this invention. Laboratory experiments demonstrated that the amount of antimicrobial composition on one or more of the following catheter surfaces: the extension lumen 182, hub lumen 179, female luer 175, proximal end 174, and the catheter threads 178, increased with multiple uses of certain embodiments of the sealing cover 141. The invention may be used to create an antimicrobial coating on the catheter hub threads, the catheter end face, the catheter luer taper, the interior channel of the hub, or combinations thereof.

Figure 6A:
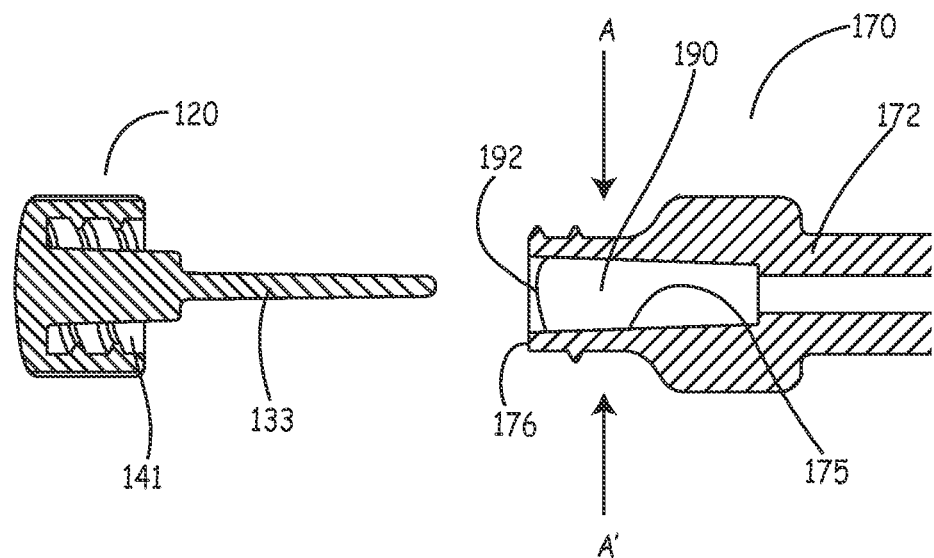
FIG. 6A is a side cross section view of a sealing cover made in accordance with an implementation of the invention, prior to the sealing cover being inserted into a catheter.
Figure 6B:
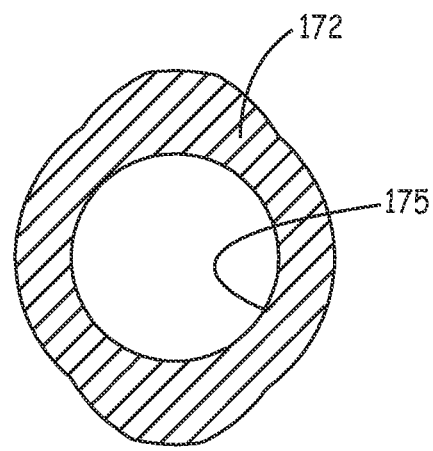
FIG. 6B is an end cross section view of the catheter of FIG. 6A.

In reference now to FIG. 6A, a side cross section view of a sealing cover 120 made in accordance with an implementation of the invention is shown, prior to the sealing cover 120 being inserted into a catheter. The sealing cover 120 includes sealing cover threads 141 and elongate member 133 configured to be inserted into the proximal end of the catheter. The elongate member 133 displaces lock solution 190, which results in the meniscus 192 being pushed out of the catheter onto the end face 176 of the catheter 170. Eventually, as the sealing cover 120 continues to be installed, the meniscus 192 (and lock solution) will travel over the sealing cover threads 141. This transfer of fluid onto the threads 141 can assist in delivering antimicrobial compositions to the threads of the catheter hub, either by transferring antimicrobial from the threads 141 to the catheter hub, or by carrying antimicrobial from the elongate member 133 (and/or the central protrusion) to the exterior of the catheter hub, including the spaces between threads on the catheter hub and threads on the sealing cover 120. FIG. 6B shows an end cross section view of the hub 172 of FIG. 6A taken along lines A-A' of FIG. 6A.

Figure 7A:
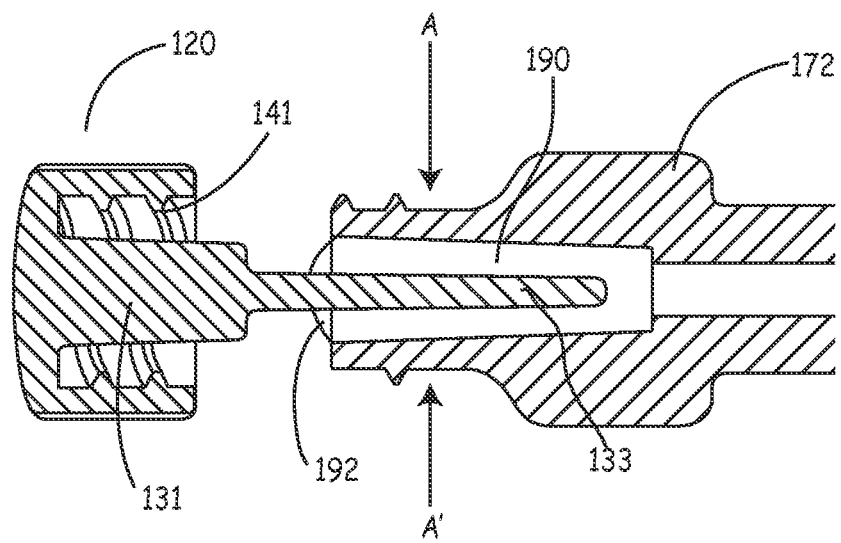
FIG. 7A is a side cross section view of a sealing cover made in accordance with an implementation of the invention, the sealing cover partially inserted into a catheter.
Figure 7B:
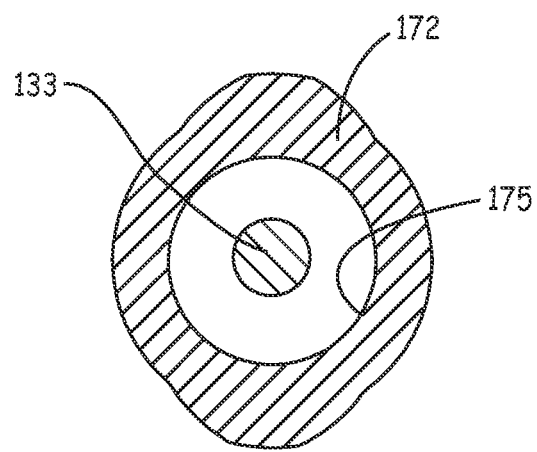
FIG. 7B is an end cross section view of the sealing cover and catheter of FIG. 7A.

In reference now to FIG. 7A, a side cross section view of a sealing cover made in accordance with an implementation of the invention is shown, the sealing cover 120 shown partially inserted into a catheter. As the sealing cover 120 is inserted into the catheter the elongate member 133 displaces lock solution 190, such as to move the meniscus 192 proximally as the lock solution 190 is displaced out of the hub 172. The sealing cover 120 can be inserted after a clamp is placed on the catheter to clamp the catheter shut; this prevents the displaced lock solution from flowing distally from the catheter and results in the displaced lock solution and meniscus 192 moving proximally. FIG. 7B shows an end cross section view of the sealing cover partially inserted into a catheter of FIG. 7A taken along lines A-A' of FIG. 7A, with the elongate member 133 partially inserted into the female luer 175.

Figure 8A:
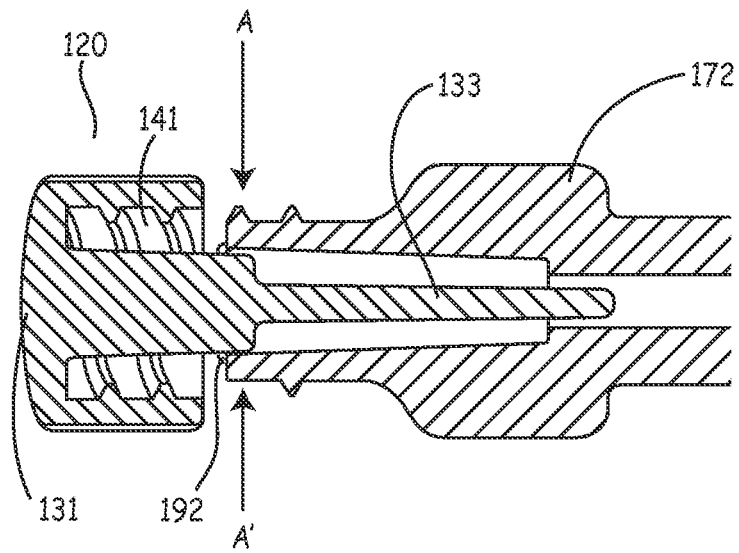
FIG. 8A is a side cross section view of a sealing cover made in accordance with an implementation of the invention, the sealing cover partially inserted into a catheter.

Referring to FIG. 8A, a side cross sectional view of a sealing cover 120 made in accordance with an implementation of the invention, the sealing cover 120 is partially inserted into a catheter. As the sealing cover 120 progresses further into the catheter more lock solution 190 is forced out, and the meniscus 192 can increase in size from the additionally displaced lock solution. The sealing cover threads 141 contacts the meniscus 192 of the lock solution 190 in the depicted embodiment, thereby either receiving antimicrobial composition from the lock solution, and/or adding further antimicrobial composition to the lock solution.

Figure 8B:
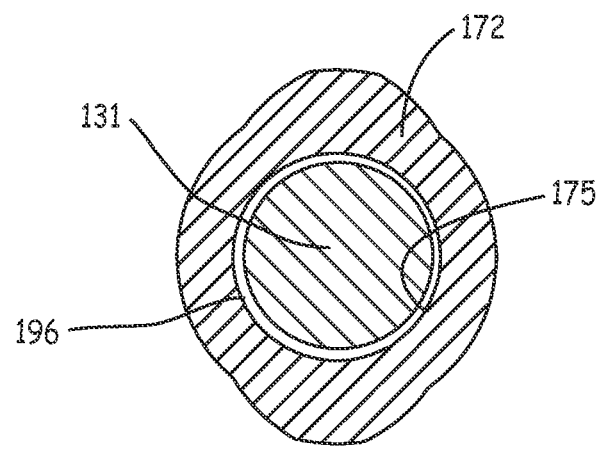
FIG. 8B is an end cross section view of the sealing cover and catheter of FIG. 8A.

Next, FIG. 8B shows a cross sectional view of the catheter and hub taken along lines A-A' of FIG. 8A. As the sealing cover 120 is inserted into the catheter a gap 196 can be defined, such as between the central protrusion 131 (formed as a male luer) and the female luer 175. The gap 196 can be at least partially occupied by lock solution 190, such as to allow lock solution 190 to pass from the catheter to the sealing cover threads 141.

Figure 9A:
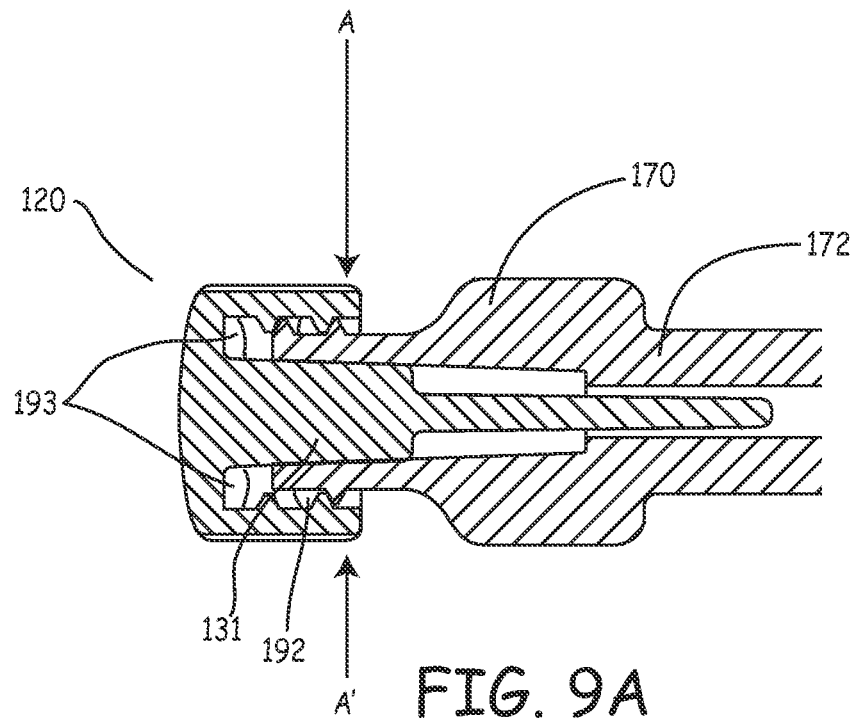
FIG. 9A is a side cross section view of a sealing cover made in accordance with an implementation of the invention, the sealing cover almost completely inserted into a catheter.
Figure 9B:
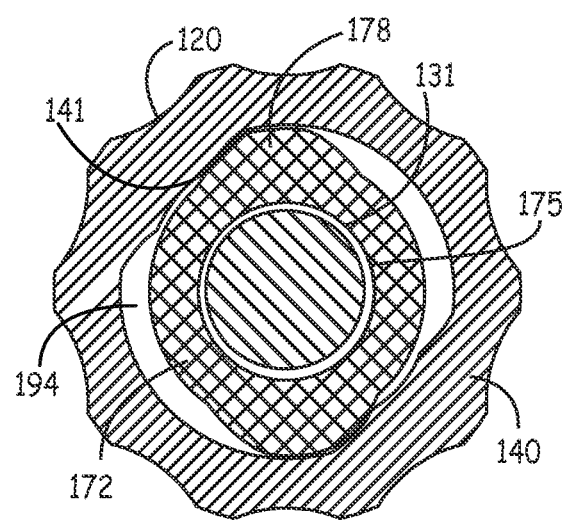
FIG. 9B is an end cross section view of the sealing cover and catheter of FIG. 9A.

FIG. 9A is a side cross section view of a sealing cover 120 made in accordance with an implementation of the invention, the sealing cover 120 almost completely inserted into a catheter. As the sealing cover 120 progresses into the catheter an air bubble 193 can form in the sealing cover, yet the lock solution 190 and minuscus 192 continue to progress to further cover the sealing cover threads 141. Further, FIG. 9B is a close-up of the side cross sectional view taken along lines A-A' of FIG. 9A. A gap 196 can be at least partially be defined between the central protrusion 131 and the female luer 175, such as to permit lock solution 291 to pass from the catheter to the sealing cover 120.

Figure 10A:
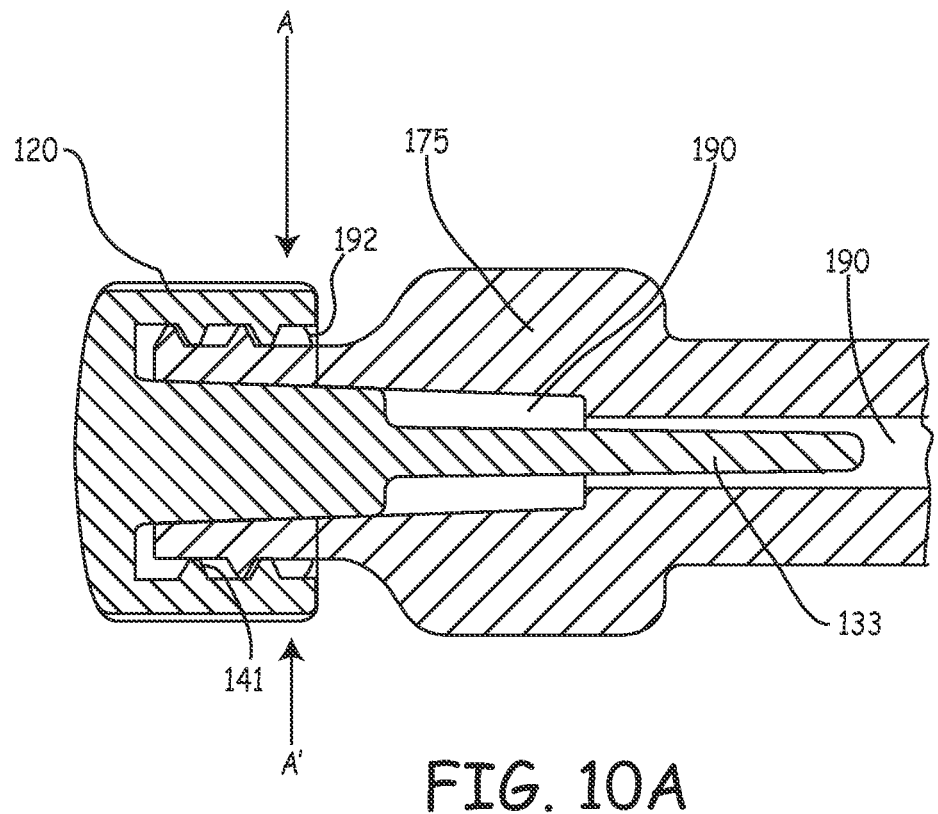
FIG. 10A is a side cross section view of a sealing cover made in accordance with an implementation of the invention, the sealing cover fully inserted into a catheter.
Figure 10B:
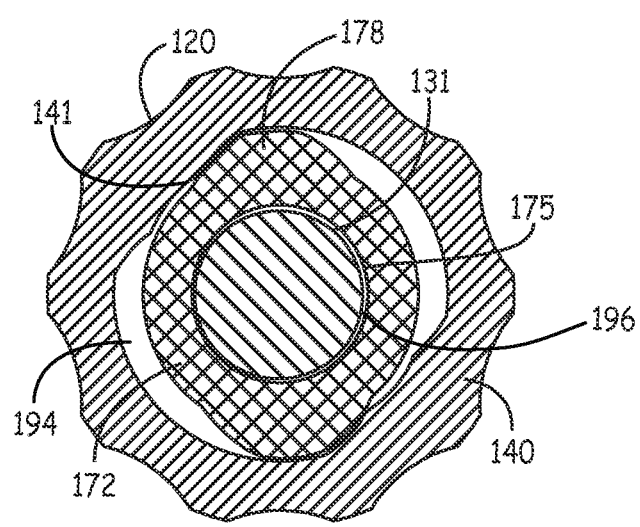
FIG. 10B is an end cross section view of the sealing cover and catheter of FIG. 10A.

In reference to FIG. 10A, a side cross section view of a sealing cover 120 made in accordance with an implementation of the invention, the sealing cover 120 fully inserted into a catheter hub. A high concentration antimicrobial composition within lock solution 190 can be located in hub 172. The lock solution can be trapped in the gap 196. The lock solution can no longer pass through the gap 196 and the lock solution is disposed on the sealing cover threads 141. In an implementation of the invention, the elongate member 131 is entirely proximal to the clamp; therefore the sealing cover 120 can be removed from the catheter while the catheter is still clamped shut. Referring to FIG. 10B, an end cross section view of the sealing cover 120 of FIG. 10A taken along lines A-A' of FIG. 10A is shown. The gap 196 can be sufficiently narrow to prevent further flow of lock solution 190 from the catheter to the sealing cover 120.

In reference to FIG. 11A, a side cross section view of a sealing cover 120 made in accordance with an implementation of the invention is shown. The sealing cover 120 does not, in this embodiment, include an elongate member. A meniscus 192 can form where the male luer defining central protrusion 131 enters the catheter. Further, FIG. 11B shows an end cross section view of the catheter hub of FIG. 11A. The female luer 175 is at least partially filled with lock solution 190. The lock solution can form a meniscus 192 where the central protrusion 131 enters the female luer 175, as shown in FIG. 11A.

Figure 12A:
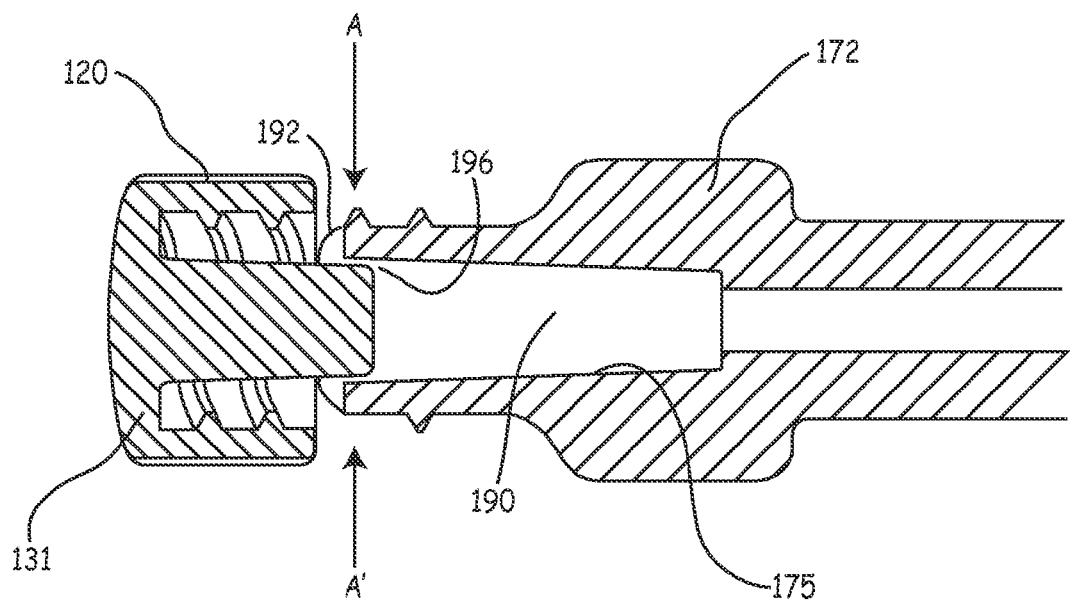
FIG. 12A is a side cross section view of a sealing cover made in accordance with an implementation of the invention, the sealing cover partially inserted into a catheter.
Figure 12B:
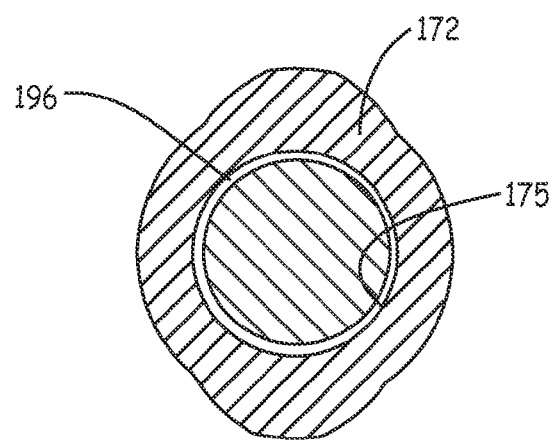
FIG. 12B is an end cross section view of the sealing cover and catheter of FIG. 12A.

In reference now to FIG. 12A, a side cross section view of a sealing cover 120 made in accordance with the implementation of FIG. 11A is shown, the sealing cover 120 partially inserted into a catheter. As the central protrusion 131 (formed as a male luer) is inserted further into the female luer 175, more lock solution 190 is displaced from the catheter and the meniscus 192 moves proximally as the volume of lock solution outside the catheter increases. Lock solution 190 can pass from the female luer to the meniscus 192 and to the sealing cover 120 through a gap 196. The gap 196 can be a passage between the central protrusion 131 (a male luer) and the female luer 175. FIG. 12B shows an end cross section view of the sealing cover of FIG. 12A. The gap 196 can be ring shaped and can permit the passage of lock solution 190 between the female luer 175 and the central protrusion 131.

Figure 13:
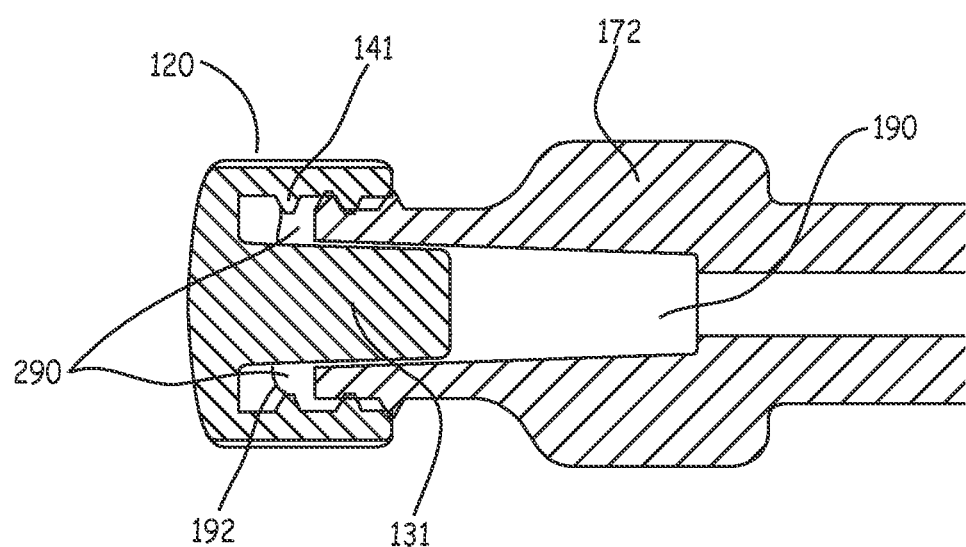
FIG. 13 is a side cross section view of a sealing cover made in accordance with an implementation of the invention, the sealing cover almost completely inserted into a catheter.

Referring to FIG. 13, a side cross section view of a sealing cover 120 made in accordance with an implementation of the invention, the sealing cover 120 almost completely inserted into a catheter hub. As the central protrusion 131 is inserted into the catheter hub, lock solution 190 is displaced from the female luer 175, such as through gap 196. The meniscus 192 can progress further along the sealing cover threads 141 as the lock solution 290 exits the catheter. A volume of lock solution 290 is located between the sealing cover threads 141 and the catheter with a surface defined by the meniscus 192.

Figure 14:
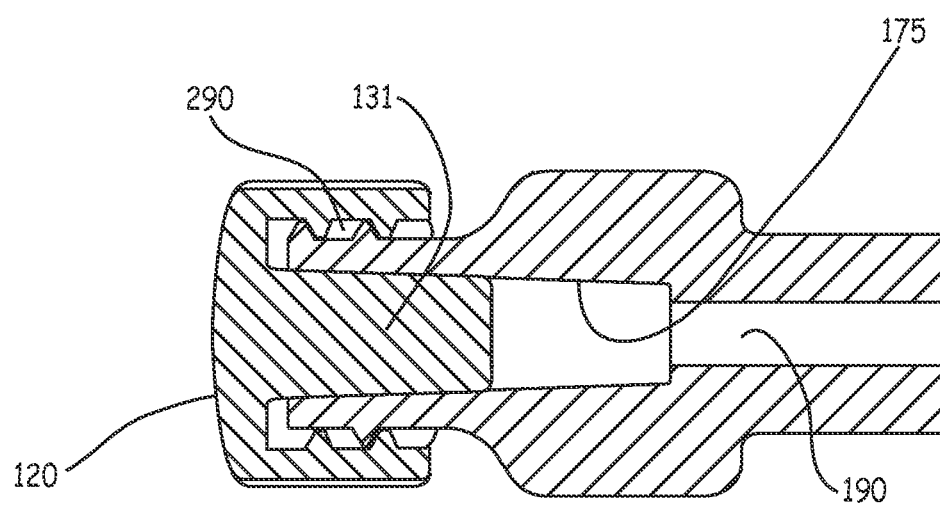
FIG. 14 is a side cross section view of a sealing cover made in accordance with an implementation of the invention, the sealing cover fully inserted into a catheter.

Further, in reference to FIG. 14, a side cross section view of a sealing cover 120 made in accordance with an implementation of the invention, the sealing cover 120 is fully inserted into a catheter. The central protrusion 131 can contact the female luer 175, such as to cause the flow of the lock solution 190 to cease. A volume of lock solution 190 can thus be located between the catheter and the sealing cover 120.

Figure 15:
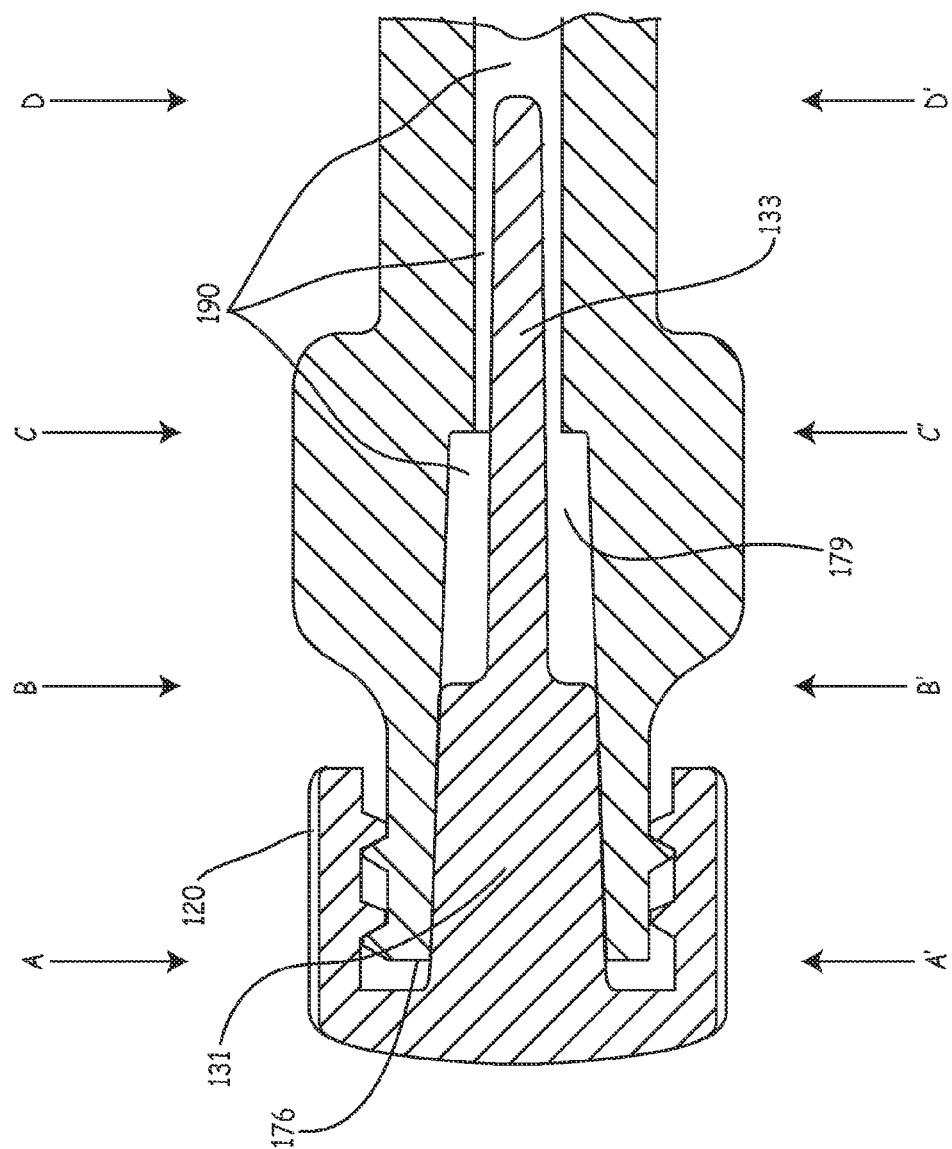
FIG. 15 is a side cross sectional view of a sealing cover made in accordance with an implementation of the invention, showing relative dimensions and volumes of the sealing cover components with the sealing cover inserted into a catheter.

In reference now to FIG. 15, a side cross sectional view of a sealing cover 120 made in accordance with an implementation of the invention, showing relative dimensions and volumes of the sealing cover 120 components within the hub lumen 179 is shown. When the hub lumen 179 is filled with a fluid, such as lock solution 190, to the end face 176, the displaced volume of fluid is equal to the volume of the central protrusion 131 in addition to the volume of the elongate member 133. Four cross-sectional planes are shown in FIG. 15: A-A'; B-B'; C-C', and D-D'. Each of these pairs of planes define volumes within the interior of the catheter. Thus, there is a volume within the catheter hub between planes A-A' and B-B'. This volume is occupied, in FIG. 15, by the central protrusion 131. A next volume is from B-B' to C-C'. This volume extends from the end of the central protrusion 131 to the end of point where the elongate member 133 enters a constriction in the lumen in the hub. A third volume is located between C-C' and D-D', this volume in the depicted embodiment has a particularly small cross sectional area, because it includes a relatively narrow portion of the lumen along with the elongate member 133 extending into the lumen, such that the volume is only the space between the elongate member and the walls of the lumen of the hub. A fourth volume, only partially shown in FIG. 15, is the volume form D-D' to the clamp positioned nearer the patient (not shown).

Upon insertion of the sealing cover into the proximal end of a transdermal catheter, the antimicrobial composition elutes into the lock solution 190. However, the configuration of the volumes, as shown in FIG. 15, is such that a large amount of the antimicrobial composition is initially contained within the volume between B-B' and C-C'. Some of this antimicrobial composition will eventually diffuse from the volume between B-B' and C-C' through the narrows between C-C' and D-D' to eventually arrive at the larger volume distal to D-D'. However, the geometry is such that the concentration in the volume B-B' to C-C' has a relatively high level for an extended period of time (in typical embodiments). This high concentration often results in precipitation of some of the antimicrobial composition onto the walls of the hub lumen between B-B' to C-C'; as well as between C-C' to D-D'. This precipitated antimicrobial composition can prolong antimicrobial activity, and can even provide protection between changes of the sealing cover 120, without exposing the patient's blood supply to high concentrations of antimicrobial compositions.

Thus in certain embodiments, upon insertion of the elongate member and tapered member of the antimicrobial delivery device into the hub, the interior of the catheter defines a first volume of lock solution (such as B-B' to C-C'), a second volume of lock solution (such as C-C' to D-D'), and a third volume of lock solution (such as D-D' to the catheter clamp), the first volume of lock solution having an average diameter greater than the average diameter of the second volume, the second volume of lock solution having an average cross sectional area less than the average cross sectional area of first volume and third volume, and the third volume of lock solution having a cross sectional area substantially equal to the average lumen cross sectional area of the catheter proximal to the clamp. In certain implementations the first volume of lock solution comprises lock solution located in the portion of the interior channel of the hub between the end of the tapered member and the end of the tapered interior surface of the interior channel; wherein the second volume of is lock solution located between the end of the tapered interior surface of the interior lumen and the end of the elongate member; and wherein the third volume of lock solution comprises lock solution located within the catheter between the end of the elongate member and the clamp. Optionally the second volume is less than the first volume, and the first volume is less than the third volume. In certain embodiments, upon insertion of the elongate member and tapered member into the hub, antimicrobial concentration in the first volume is initially higher than antimicrobial concentrations in the third volume. In certain embodiments, the antimicrobial concentration in the first volume after 48 hours is at least ten times higher than the antimicrobial concentration in the third volume. In certain embodiments, the amount of antimicrobial in the first and second volumes after 48 hours is at least three times higher than the amount of antimicrobial in the third volume.

In one embodiment a syringe can be used to fill the hub lumen 179, if the syringe is removed without injecting additional fluid as the syringe is removed, the hub volume will be under filled by the protrusion of the syringe. In that case the displaced volume is equal to the volume of the central protrusion 131 in addition to the volume of the elongate member 133, and minus the volume of the protrusion of the syringe. In an embodiment the volume of the protrusion of the syringe is 0.070 mL. In an embodiment the volume of the central protrusion is 0.074 mL. In an embodiment the volume of the elongate member is 0.053 mL. In an embodiment the volume of the thread region of the sealing cover 120 is 0.034 mL. It is desirable to wet the threads of the retaining ring and the hub with the displaced lock solution; to ensure wetting of the threads in this embodiment, the elongate member has a volume equal to or greater than 0.030 mL.

Figure 16A:
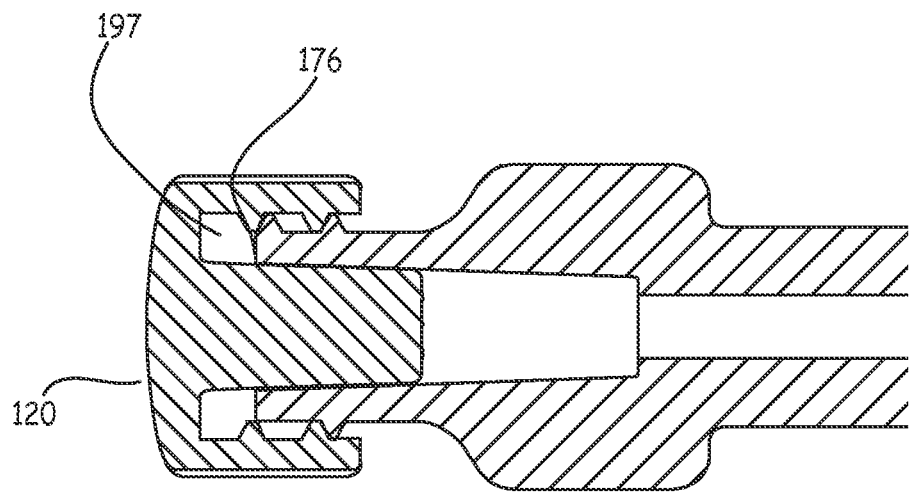
FIG. 16A is a side cross sectional view of a sealing cover made in accordance with an implementation of the invention, with the sealing cover inserted into a catheter.
Figure 16B:
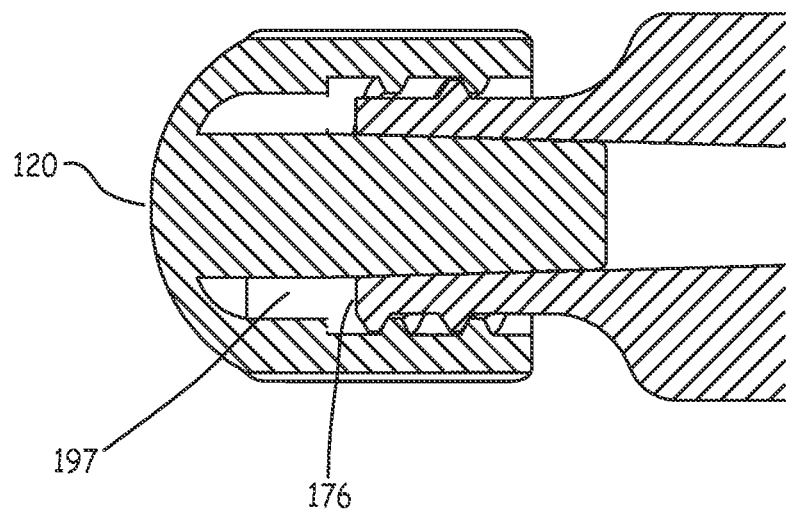
FIG. 16B is a side cross sectional view of a sealing cover made in accordance with an implementation of the invention, with the sealing cover inserted into a catheter.

FIG. 16A is a side cross sectional view of a sealing cover made in accordance with an implementation of the invention, showing a gap 197 between the end face 176 of the hub of the catheter and the cover 120. FIG. 16B is a side cross sectional view of a sealing cover made in accordance with an implementation of the invention, also with a gap 197 at the end face 176 of the catheter and the sealing cover 120.

Figure 17:
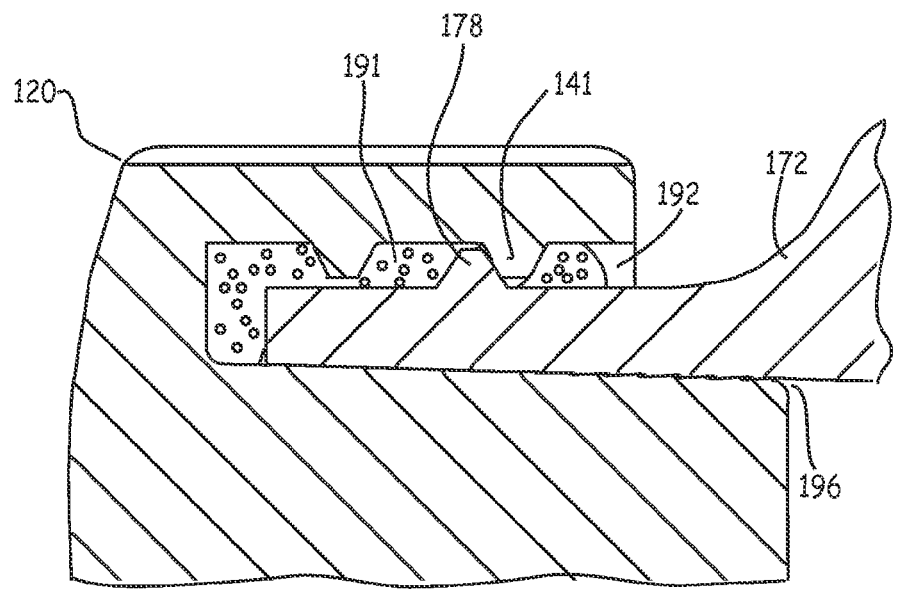
FIG. 17 is a side cross sectional view of a sealing cover made in accordance with an implementation of the invention, showing fluid on the threads of the proximal end of the catheter.

In reference now to FIG. 17, an enlarged side cross sectional view of a sealing cover 120 is shown; the sealing cover 120 is made in accordance with an implementation of the invention, showing fluid on the threads of the proximal end of the catheter. As the sealing cover 120 was inserted into the catheter 170, a meniscus 192 of lock solution 191 can form. Lock solution 191 containing an antimicrobial composition can be located between the sealing cover threads 141 and the catheter threads 178.

Figure 18:
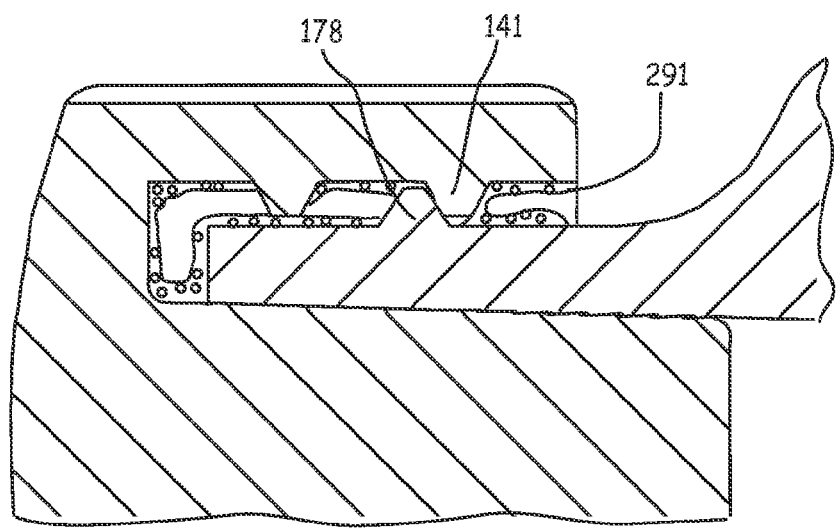
FIG. 18 is a side cross sectional view of a sealing cover made in accordance with an implementation of the invention, showing at least a portion of the fluid of FIG. 17 having evaporated to leave an antimicrobial residue.
Figure 19:
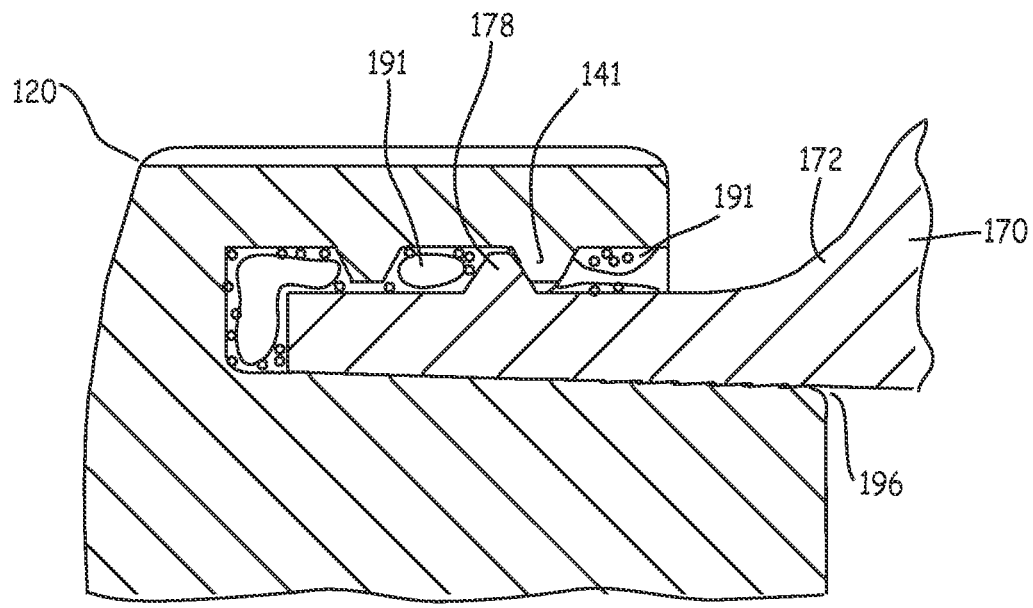
FIG. 19 is a side cross sectional view of a sealing cover made in accordance with an implementation of the invention, showing rehydration of a portion of the antimicrobial residue of FIG. 18.
Figure 20:
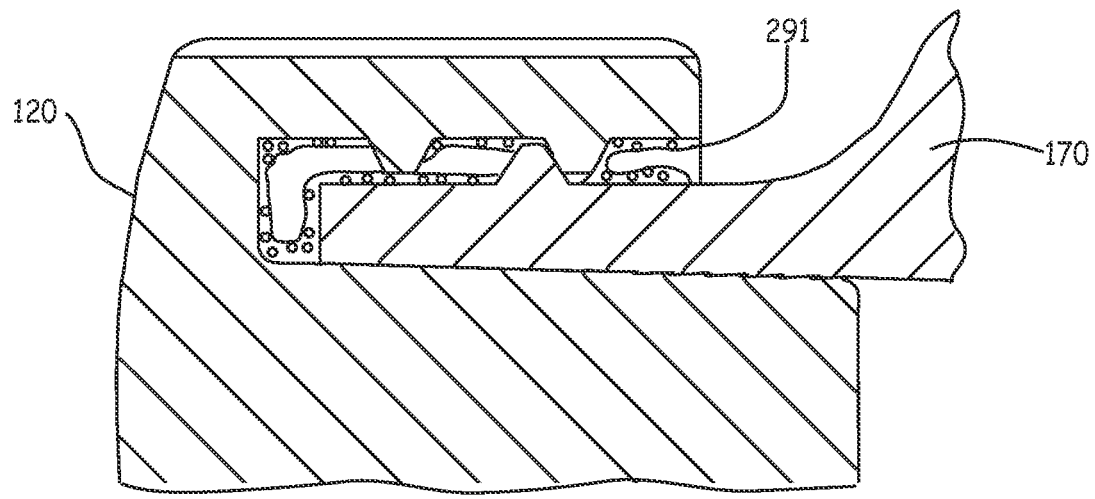
FIG. 20 is a side cross sectional view of a sealing cover made in accordance with an implementation of the invention, showing at least a portion of the fluid of FIG. 19 having evaporated, leaving an antimicrobial residue.

Referring to FIG. 18, a side cross sectional view of a sealing cover made in accordance with an implementation of the invention, showing at least a portion of the fluid of FIG. 17 having evaporated leaving an antimicrobial residue is shown. With the passing of time, the lock solution 191 can evaporate leaving antimicrobial residue 291 on and between the sealing cover threads 141 and the catheter threads 178. FIG. 19 is a side cross sectional view of a sealing cover made in accordance with an implementation of the invention, showing rehydration of a portion of the antimicrobial residue of FIG. 18. As shown in FIG. 19, FIG. 20 is a side cross sectional view of a sealing cover made in accordance with an implementation of the invention, showing at least a portion of the fluid of FIG. 19 having evaporated leaving an antimicrobial residue. As shown in FIG. 20, antimicrobial residue 291 is retained both on the threads of the sealing cover and on the catheter threads.

Figure 21:
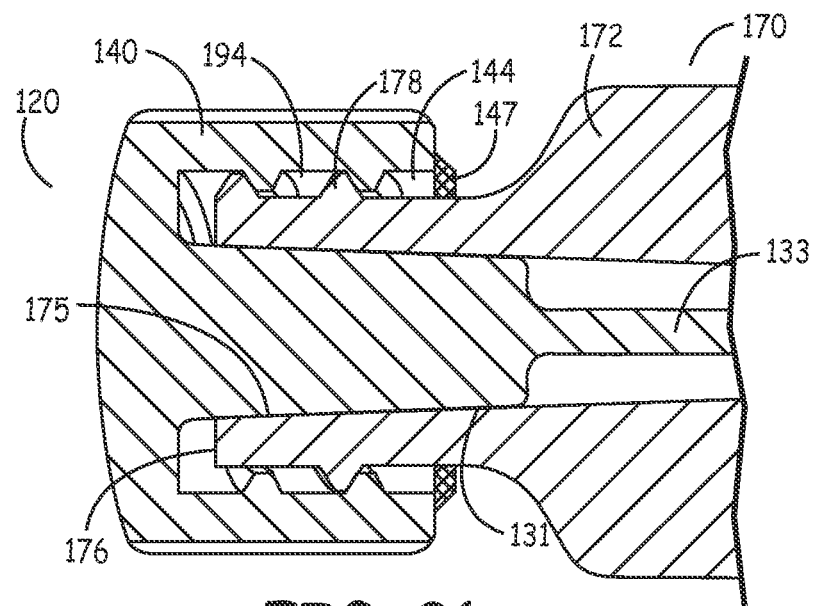
FIG. 21 is a side cross-section view of a sealing cover with a seal at the distal end of a retaining ring made in accordance with an implementation of the invention, the sealing cover installed onto a catheter.

In reference to FIG. 21, a sealing cover 120 is shown fully inserted into a catheter 170. This embodiment contains an end seal 147. The end seal 147 provides additional benefit by preventing organisms from entering the distal opening 144 thereby preventing the organisms from subsequently progressing through the void 194 where they could then contaminate the end face 176 and female luer 175. Reducing the number of organisms that can enter distal opening 144 can further reduce the incidence of CRBSI. The end seal 147 can be made of an elastic material so it is sealing coverable of stretching over the catheter threads 178 while the sealing cover 120 is being inserted, and it should also conform to the shape of the hub 172 so it creates an effective organism-blocking seal. The end seal 147 is preferably made of a durable material so it does not rip or tear. It should generally be thin and flexible enough so it is easy to insert. The end seal 147 allows fluid to escape as the sealing cover 120 is being inserted onto the catheter 170, yet acts as a barrier to substantially retain the lock solution that was pushed into the void 194 during insertion. In the preferred embodiment, this is accomplished by keeping the wall thin and flexible enough to allow the increased pressure to escape where the end seal 147 contacts the hub 172. In an example embodiment, the end seal 147 is over molded onto the retaining ring 140. A thermoplastic elastomer, such as Exxon Mobile's Santoprene, can be used. However, other materials, such as silicone, may be suitable. In an embodiment, the end seal 147 is in the range of 0.005 inch to 0.100 inch thick. In another embodiment, the end seal 147 is in the range of 0.010 inches to 0.040 inches thick.

The lock solution in void 194 also acts as a barrier to organism infiltration. It contains antimicrobial composition that has dissolved from the sealing cover 120 surfaces (elongate member 133, central protrusion 131, and catheter threads 178). In a desired embodiment, the antimicrobial levels result in an antimicrobial concentration that is highly effectively at killing a broad spectrum of organisms.

Figure 22:
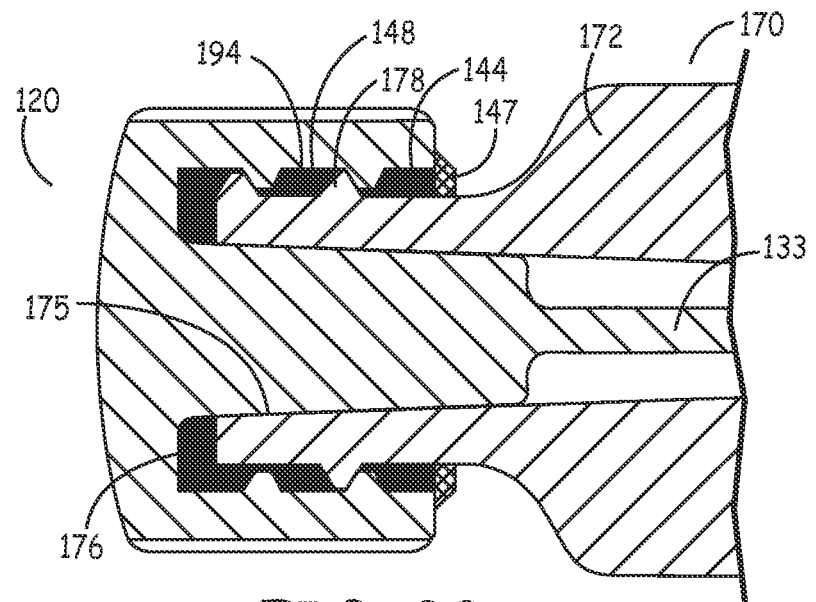
FIG. 22 is a side cross-section view of a sealing cover with foam along the threads of a retaining ring made in accordance with an implementation of the invention, and the sealing cover installed onto a catheter.

In reference to FIG. 22, the sealing cover 120 is shown fully in cross section inserted into a catheter 170. This embodiment can contain a thread seal 148 that is impregnated with an antimicrobial composition in the same amount as (and in place of) the amount on the sealing cover threads 141 of FIG. 5C. The thread seal 148 provides additional benefit by preventing organisms from entering the distal opening 144 and, since the void 194 is now occupied with the thread seal 148, it prevents organisms from progressing through the occupied void 194 where they would otherwise contaminate the end face 176 and female luer 175. Reducing the number of organism that can enter distal opening 144 can further reduce the incidence of CRBSI.

The thread seal 148 is preferably made of an elastic foam material that is sealing coverable of conforming around the catheter threads 178 while the sealing cover 120 is being inserted, and it should also conform to the shape of the hub 172 so it creates an effective organism-blocking seal. The most distal end of the thread seal 148 often has a thin layer of closed polyurethane to help reduce evaporation of the solution. The thread seal 148 is desirably made of a durable material so it does not rip or tear. One aspect of the thread seal 148 is that it allows fluid to cover the thread seal 148 as the sealing cover 120 is being inserted into the catheter 170, yet it acts as a barrier to substantially retain the lock solution that was pushed into the filled void 194 during insertion. In the preferred embodiment, this is accomplished by manufacturing the thread seal 148 out of an open cell hydrophilic medical polyurethane foam and having a thin layer of solid polyurethane at the most distal end of the thread seal 148. The thread seal 148 and the antimicrobial composition incorporated therein also acts as a barrier to organism infiltration. It contains antimicrobial composition that has dissolved from the sealing cover 120 surfaces (such as one or more of the elongate member 133, central protrusion 131, and thread seal 148).

Figure 23A:
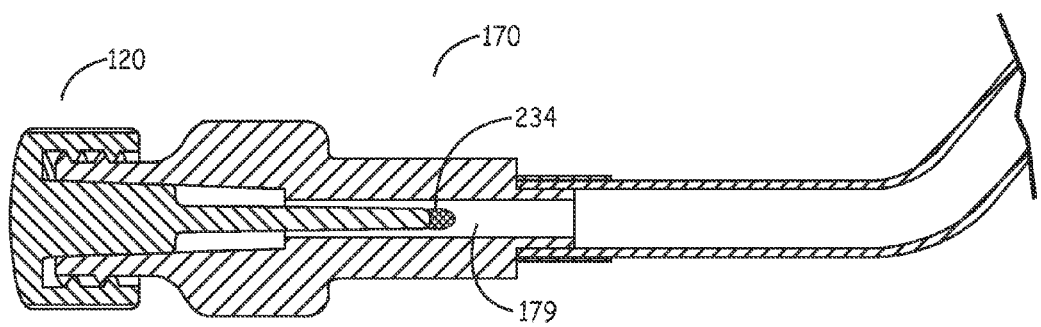
FIG. 23A is a side cross-section view of a sealing cover with a swellable tip made in accordance with an implementation of the invention, installed onto a catheter. The tip is shown in its unswollen state.

FIG. 23A refers to an alternative embodiment of the sealing cover 120 which possesses a tip 234 that has a diameter that is smaller than the diameter of the hub lumen 179 when the tip 234 is inserted into a catheter 170, but subsequently expands in size. This embodiment is especially beneficial when the sealing cover 120 is used in a catheter 170 that does not have a clamp for confining the solution, or in cases where it is desirable to further limit the amount of antimicrobial composition required (less is required because the volume of confined solution is lower). The tip 234 is shown in FIG. 23A in its unswollen state during insertion in order to allow the elongate member to be easily inserted and to minimize its potential for pushing organisms distal to the tip 234 by a plowing action. The elongate member in a preferred embodiment remains sufficiently stiff while it is being inserted onto into the catheter 170 and it does not require any extra parts or aids for insertion.

Figure 23B:
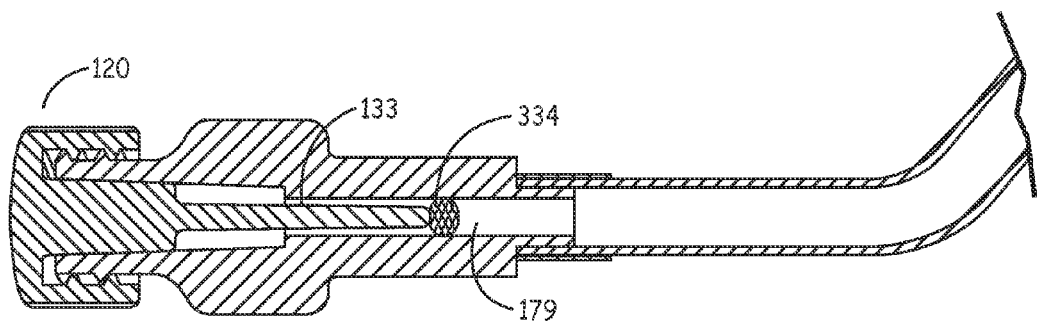
FIG. 23B is a side cross-section view of a sealing cover with a swellable tip made in accordance with an implementation of the invention, installed onto a catheter. The tip is shown in its swollen state.

FIG. 23B refers to an alternative embodiment of the sealing cover 120 as described in reference to FIG. 23A, except the tip 334 is shown in its swollen state. In the depicted embodiment the diameter of the tip 334 is equal to the diameter of the hub lumen 179 in its swollen state; the tip 334 preferably conforms to the surface of the hub lumen 179 as it swells. The swollen tip 334 is beneficial for confining the solution, or in cases where it is desirable to further limit the amount of antimicrobial composition required (less is required because the volume of confined solution is lower). The tip 334 is removable from the hub lumen 179 when reasonable removal force is applied to the sealing cover 120. This is achieved by choosing the material and size the tip 334 such that, when it is in its swollen state, the normal force that the tip 334 applies to the wall of the hub lumen 179 is sufficiently low to allow acceptable removal force. In an example embodiment the diameter of the unswollen tip 234 (reference FIG. 23A) is 0.060 inches, the diameter of the confined swollen tip 334 is 0.098 inches (the same diameter as the hub lumen 179), and the diameter of the unconfined swollen tip is 0.110 inches when placed in normal saline. However, these diameters will vary to match the diameter of the device that the sealing cover is being used with. The preferred unconfined swollen diameter (defined as the diameter the tip will expand to if it is not confined by a lumen wall) is slightly larger than the diameter of the hub lumen 179. An additional beneficial effect of the swollen tip is that it produces a scrubbing effect on the catheter wall that will physically remove organisms adhered to the interior wall section upon removing the sealing cover from the catheter.

In one embodiment, the tip is manufactured to produce anisotropic swelling, such that the diameter increases but the length does not substantially increase. In another embodiment the entire elongate member is made of an anisotropically swelling material such that the diameter increases but the length does not substantially increase.

In one implementation, the material of the tip 334 consists of a swellable polyurethane, such as Lubrizol TG-500, that has been heat fused onto the elongate member 133 which is a non-swellable polyurethane, such as Lubrizol 1065D. These materials provide acceptable swelling, durability, strength and flexibility. The elongate member is coated with antimicrobial composition in an amount sufficient to obtain an adequate antimicrobial effect, yet low enough to remain safe for the patient.

Figure 24:
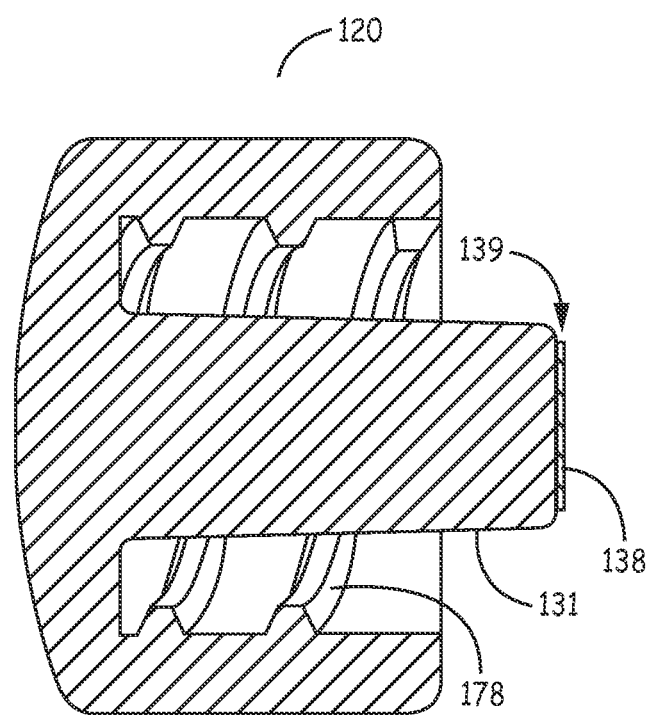
FIG. 24 is a side cross-section view of a sealing cover constructed without an elongate member made in accordance with an implementation of the invention.

In reference to FIG. 24 this alternative embodiment of the invention is useful in applications where an elongate member will not fit into a catheter because the internal diameter of the catheter is too small, such as with peripherally inserted central catheters (PICC). In this embodiment, the sealing cover 120 does not contain an elongate member as in previous embodiments. Instead, the sealing cover has a luer end face 138 that is flat or slightly recessed, and the end face 138 is coated with an antimicrobial layer 139. The preferred type and amount of antimicrobial in the antimicrobial layer 139 is the same as the elongate member (reference the description for FIG. 5C). Similarly, the central protrusion 131 and the catheter threads 178 preferably contain the same type and amount of antimicrobial composition as the other embodiments. The antimicrobial composition is preferably applied to the end face using a precision metering pump with 15% chlorhexidine acetate in a methanol solution. Other solvent, percentages and coating methods may be used.

Figure 25A:
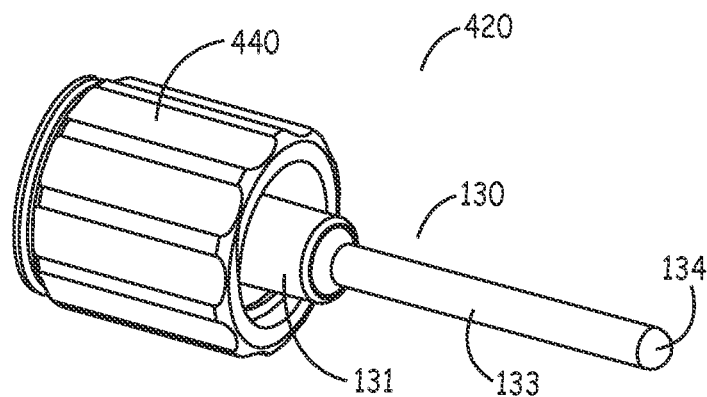
FIG. 25A is a perspective view of a sealing cover made in accordance with an example implementation of the invention.

In reference to FIG. 25A, an alternative embodiment of the invention is shown in which the sealing cover 420 is manufactured from two components, a retaining ring 440 and an insert 130. It is desirable to have a highly controlled and repeatable amount of antimicrobial composition placed upon the desired regions of the sealing cover 420. It is also preferred to have different amounts of antimicrobial on the different regions. It becomes easier to coat each region of the sealing cover 420 if the retaining ring 440 is not blocking access to the central protrusion 131 (and vice versa). This is accomplished by manufacturing the sealing cover 420 as two separate pieces, the retaining ring 440 and the insert 130. The preferred amount of antimicrobial composition within each region remains the same as presented above (refer to Ref 5C).

Figure 25B:
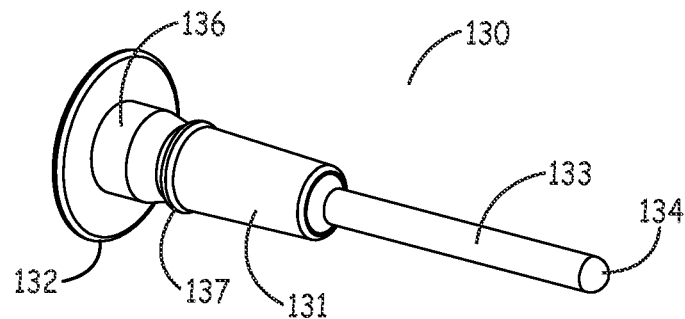
FIG. 25B is a perspective view of an insert made in accordance with an example implementation of the invention.
Figure 25C:
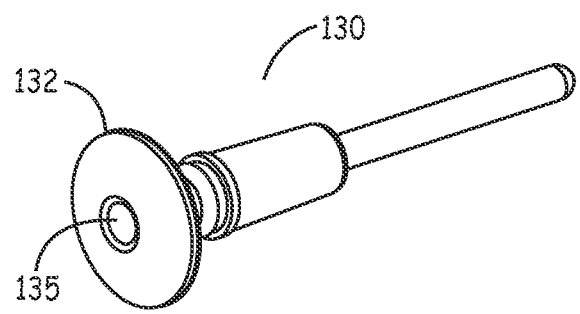
FIG. 25C is a perspective view of an insert made in accordance with an example implementation of the invention.

In reference to FIG. 25B, the insert 130 is coated with chlorhexidine acetate the elongate member 133 and along the central protrusion 131. The plate 132, sealing cover shoulder 136, and the retaining flange 137 do not require coating. The two parts that are coated are the central protrusion 131 and the elongate member 133; contain the same amount of antimicrobial as referenced above In reference to FIG. 25C, the plate 132 at the proximal end of the insert 130 has a hole 135. The purpose of this hole 135 is to improve manufacturing. For instance, the hole 135 creates a convenient feature that can be used for holding and rotating the insert 130 to allow the part to be spun as it is being coated. The hole 135 also reduces shrinkage in the injected molded insert 130 by creating more uniform wall thickness.

Figure 25D:
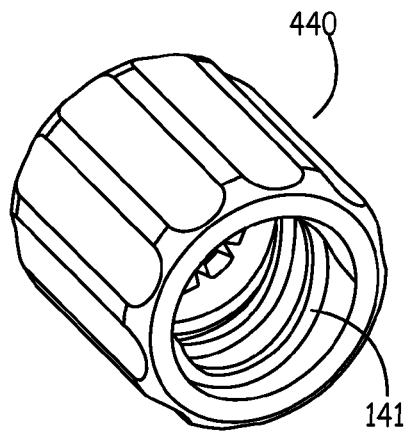
FIG. 25D is a perspective view of a retaining ring made in accordance with an example implementation of the invention.

In reference to FIG. 25D, the retaining ring 440 is a commercially available product from Value Plastics, Inc. with the exception that the sealing cover threads 141 are coated with an antimicrobial composition. The antimicrobial composition in the preferred embodiment is chlorhexidine acetate in the same preferred amount as disclosed above. The retaining ring 440 is readily coated using a spraying technique where the retaining ring 440 is spun along its axis, and the antimicrobial is sprayed directly onto the sealing cover threads. As an alternative coating method, the sealing cover threads 141 were coated by filling the internal portion of the ring 440 with 7% chlorhexidine methanol solution, subsequently draining the solution and allowing the parts to dry. This resulted in approximately 1.2 mg of chlorhexidine acetate on the sealing cover threads 141. The dose of antimicrobial may be adjusted by adjusting the solution concentration.

Figure 25E:
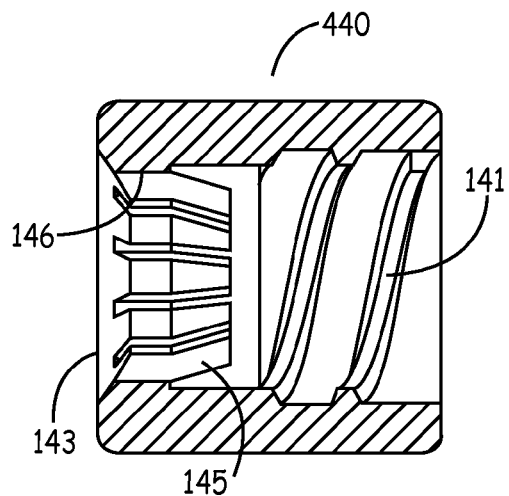
FIG. 25E is a side section view of a retaining ring made in accordance with an example implementation of the invention.

In reference to FIG. 25E, the retaining shoulder 146 comes into contact with the insert (not shown) when the insert is inserted inside the retaining ring 440. The proximal opening 143 is used to initially receive the insert 130 (refer to FIG. 10F) during assembly. The retaining fingers 145 are designed to retain the retaining ring 440 onto the insert, as will be described in the reference below. The ring shoulder 146 helps secure the insert.

Figure 25F:
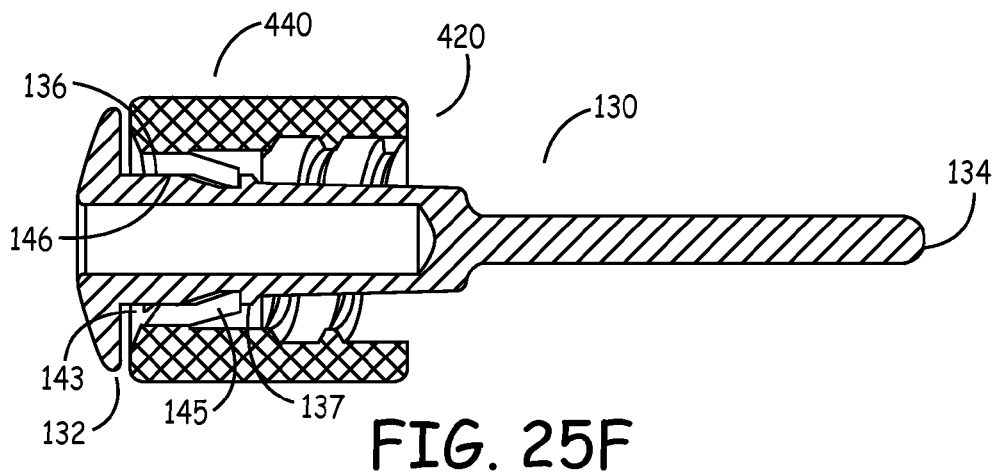
FIG. 25F is a side cross section view of a sealing cover made in accordance with an example implementation of the invention.

In reference to FIG. 25F, the preferred embodiment for the two-piece sealing cover 420 is shown. The insert 130 is shown fully inserted into the retaining ring 440. The tip 134 was pushed through the proximal opening until retaining ring 440 bottomed out on the plate 132. The retaining fingers 145 are engaged with the retaining flange 137 to secure the retaining ring 440 on the insert 130.

Figure 26:
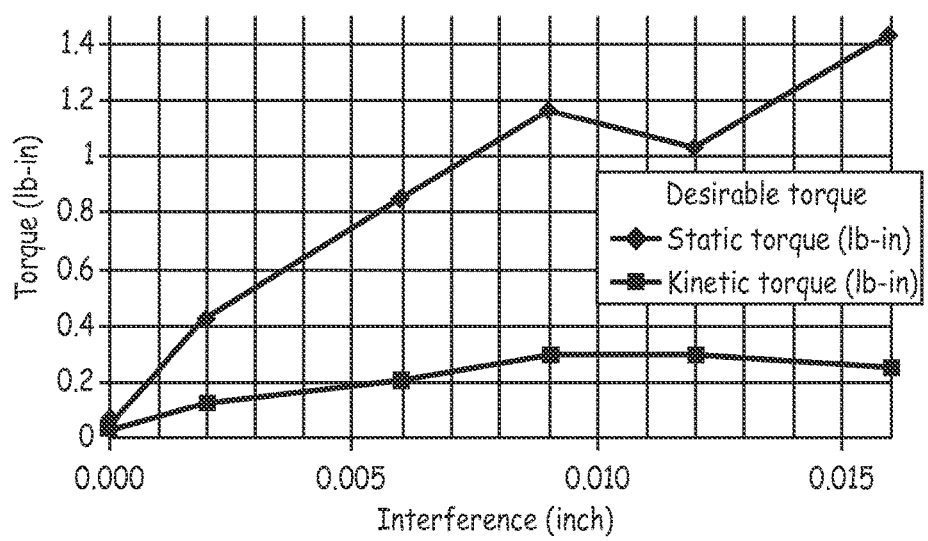
FIG. 26 is a table showing the effect of interference between a retaining ring and shoulder upon ring-insert torque.

It is desirable to have the retaining ring 440 not rotate freely on the insert 130. Instead, it is preferred to have the torque be greater than 0 pound-inches (lb-in) but less than 2.0 lb-in. In a more preferred embodiment, the torque is between 0.1 lb-in and 1.25 lb-in. In the most preferred embodiment, the torque is between 0.2 lb-in and 0.5 lb-in. By controlling the diameter of the insert shoulder 136 such that it interferes with ring shoulder 146, the torque can be controlled as shown in the graph depicted in FIG. 26.

It is preferred to keep the interference between the ring shoulder 146 and the insert shoulder 136 within the range of 0.002 inch and 0.009 inch in order to keep the rotation torque within an acceptable range.

Antimicrobial Composition

An antimicrobial composition can be incorporated both into the elongate member material and/or on the elongate member surface of the present invention. In a preferred embodiment, the antimicrobial composition is chlorhexidine acetate; approximately 250 µg of chlorhexidine acetate is coated onto a 17 mm long×1.9 mm diameter rod-shaped elongate member, resulting in a chlorhexidine acetate layer approximately 2 µm thick along. The luer portion is coated with 50 µg of chlorhexidine acetate, resulting in a layer that is approximately 0.4 µm thick. It is also possible to inject an antimicrobial composition into the catheter using a syringe, or to deliver antimicrobial compositions by way of the connector tip cavity (dry dissolvable amount, applicable for Citrate or others requiring large amounts of antimicrobial composition).

The elongate member has the added benefit of displacing fluid from within the catheter as it is inserted, transferring the solution to the outer proximal region of the catheter connector (end face and threads). Antimicrobial composition from the sealing cover dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, is the chlorhexidine acetate or other antimicrobial composition may be delivered by a coating on a luer tip (such as 250 µg of chlorhexidine acetate in a layer that is approximately 20 µm thick).

An antimicrobial composition is located on the outer surface of the elongate member, the male luer connector, and the retaining ring. The antimicrobial composition elutes from the elongate member after insertion of the elongate member/rod into a catheter. When the system is inserted into the catheter, the antimicrobial composition dissolves into the fluid contained within the catheter, thus coming into contact with infectious organisms that might be present along the connector surfaces and lumen wall of the catheter or in solution. Additionally, the antimicrobial composition and any infectious organisms are confined together in the small space along within the catheter. Another benefit is that the confining action of the clamp traps any infectious microbes within the catheter and prevents them from being transmitted to other areas of the catheter or to the body to prevent a systemic infection.

The antimicrobial compositions should kill and/or provide stasis of Gram-positive and Gram-negative bacteria and fungi. The agents may also have efficacy at killing organisms within an established biofilm and/or degrading the extracellular matrix of the film. However, this is not necessary for the invention to be beneficial because the invention is designed to kill organisms before they have an opportunity to form a biofilm. The preferred antimicrobial composition is chlorhexidine acetate, also known as chlorhexidine diacetate. Other compounds containing chlorhexidine may be used (such as chlorhexidine free base, chlorhexidine gluconate and chlorhexidine with dyes). Chlorhexidine acetate has an advantage over chlorhexidine gluconate because the risks associated with para chloroaniline may be minimized. Other suitable antimicrobial compositions may also be used. In general, the preferred antimicrobials are soluble in water, they have a history of clinical use with a demonstrated safety profile, they are antibiotic-free, they can be applied onto a medical device, and they can be subsequently dissolved into a composition having an effective concentration to inhibit growth of bacterial and fungal organisms. Suitable materials include chlorhexidine, chlorhexidine salts (such as chlorhexidine acetate or chlorhexidine gluconate), tetrasodium ethylenediaminetetraacetic acid (tetrasodium EDTA), sodium citrate (yielding a concentration of 30% or higher), iodine, taurolidine, disodium EDTA, silver compounds (including silver nanoparticles and ions), silver sulfadiazine, and, triclosan.

While one particular drug or antimicrobial composition may provide relief from a wide range of challenging organisms that could potentially lead to catheter-related bloodstream infection, two or more agents may be used to increase efficacy against a broad range of infectious organisms (bacteria and fungi).

In particular, catheter-related infections arise from three broad classes of organisms: fungi, Gram-negative bacteria, and Gram-positive bacteria. If an antimicrobial composition can be identified that would abate one or two of these types of organisms, while this would certainly be beneficial, it would leave the patient vulnerable to the remaining type(s). By pairing agents with different modes of action, infections by an increased spectrum of organisms can be prevented. This synergy would likely lead to further decreases in catheter-related morbidity and mortality, lessening the impact of the implanted catheter on the patient's quality of life. The preferred combinations of antimicrobial compositions are chlorhexidine acetate and EDTA, silver sulfadiazine and sodium dodecyl sulfate, and silver sulfadiazine and methylene blue.

Although treating, preventing, and eliminating infectious organisms for the prevention of infections is the primary use of the sealing cover, ancillary benefits can also be envisioned which would involve incorporating additional agents. An antithrombotic agent eluting from the elongate member can be used to improve the action of the heparin used currently in the lock solution. An enzyme or agent which promoted degradation of the extra-cellular matrix of biofilm (generally composed of polysaccharides) could enable use of the sealing cover for treatment as well as prevention.

In principle, antibiotics (rifampin, minocycline, etc.) can be incorporated into the sealing cover or similar device and be as effective as non-antibiotic antimicrobials. However, continuous exposure to one antibiotic can lead to antibiotic resistant bacteria strains, for example, methicillin resistant *S. aureus* (MRSA). Therefore, the preferred embodiment uses an antimicrobial composition selected from the subset of those which are not antibiotics. If, for some reason, an antibiotic is used, the risk of developing antibiotic resistant strains of bacteria may be mitigated by preparing a second, complimentary, sealing cover containing a different antibiotic. By using the two sealing covers in an alternating fashion with successive dialysis treatments, infectious organisms that are resistant to one antibiotic may be killed by the other.

When the elongate member is inserted into the hub, it creates a constriction within the interior channel of the hub which helps reduce diffusion of the antimicrobial composition and organisms from the hub to the more distal portions of the catheter. Since a large percentage of organisms are believed to enter the catheter at the hub, it is important to kill organisms in this region before they have an opportunity to spread throughout the catheter. The restriction created by the elongate member within the hub is effective at creating a confinement within the hub region. For example, the invention was manufactured using injection molding such that the tapered luer member and the elongate member were rigidly affixed to one another as a single piece of polymer. The diameter of the elongate member was 0.078 inch, and the diameter at the narrowest section of the hub channel was 0.100 inch. In this embodiment, inserting the elongate member into the hub reduced the cross-sectional area of the channel by over 60%, and creates a substantially greater reduction in diffusion.

After injection molding, the tapered member and the elongate member were subsequently coated with 60 µg and 225 µg of chlorhexidine acetate, respectively. The length of the elongate member was 0.700 inches. With the device fully inserted into a catheter, the elongate member extended along the hub's interior channel, and the elongate member ended near the end of the hub. Since the elongate member remained substantially within the hub, the elongate member was readily inserted into the catheter even when the catheter clamp was placed in its most proximal position.

A series of tests were performed using the above described embodiment. In one experiment, catheters were filled with lock solution and the devices were inserted. The catheters and devices were left for 48 hours. After the 48 hours, the devices were removed from the catheters and the amount of chlorhexidine within the hub region and within the remainder of the catheter region as measured for each of the catheters. The results demonstrated that the invention is highly effective at maintaining the chlorhexidine within the hub region. On average, over 80% of the chlorhexidine remained in the hub region after 48 hours; 20% was in the distal region of the catheter. The experiment was repeated at various antimicrobial doses and within heparin and saline lock solutions. A total of 50 devices were tested and similar results were obtained. In another experiment, the above described embodiment was placed into catheters that had been filled with a lock solution containing approximately 200,000 colony forming units per catheter of a difficult to kill microorganism, *Pseudomonas aeruginosa*. After 48 hours the devices were removed from the catheters. The catheters were then tested for the presence of the microorganism. All microorganisms were killed in all of the catheters, further demonstrating the effectiveness of the invention.

Experiments have been conducted to examine the performance of an example embodiment of the invention, which is called "Pursuit Vascular's ClearGuard HD" or the "ClearGuard HD". These experiments demonstrate that the ClearGuard HD is effective at substantially reducing organisms within catheters as intended. Two of the experiments are highlighted below.

In an experiment conducted at Pursuit Vascular, coated sealing covers were effective at consistently transferring more than 50 µg of chlorhexidine acetate (also referred to as chlorhexidine diacetate) onto the catheter's threads with a single connection. Such transfer provides the catheter with a means of further reducing infection-causing organisms which is replenished with every use of the invention. 10 µg or more of chlorhexidine is effective at reducing bacteria and other infection-causing organisms at the threads, and further preventing the organisms from infiltrating the catheter's connector end face, luer and lumen. Chlorhexidine acetate has a wide safety profile when used outside the catheter where there is little risk of it entering the bloodstream. A preferred range of chlorhexidine on the sealing cover threads is 100 µg to 2500 µg. 500 µg to 1200 µg is more preferred.

For instance, if using a chlorhexidine based antimicrobial, approximately 50 µg of chlorhexidine acetate can be effective in some embodiments. This was demonstrated in an experiment conducted at Pursuit Vascular in which 50 µg of chlorhexidine was coated on the sealing cover's luer portion. The sealing covers containing the coated luers killed all of the *Candida albicans* that were seeded within the catheter's luer region. Within the same experiment, the *Candida albicans* remained viable when uncoated sealing covers were used. Greater than 5 µg chlorhexidine acetate on the luer region is effective; 10 µg to 300 µg is preferred, and 30 µg to 80 µg is most preferred.

Laboratory testing conducted for Pursuit Vascular, Inc. demonstrated that 250 µg of chlorhexidine acetate on the elongate member produces greater than a 10,000× reduction in number of infection-causing organisms when the sealing cover is used in a standard hemodialysis catheters containing saline, heparin-saline, or saline with 4% sodium citrate. The safety profile of the invention can be enhanced by limiting the amount of chlorhexidine acetate available to enter the bloodstream, the preferred maximum amount of chlorhexidine acetate on the elongate member is 2000 µg, more preferred is 1000 µg, and most preferred is 350 µg.

Experiment 1

The objective of this experiment was to assess the antimicrobial effectiveness of Pursuit Vascular's ClearGuard HD device in the most difficult clinically-relevant model. Since the ClearGuard HD is intended to be placed in catheter hubs, but not extend into the extension tubing, the catheter model was chosen to be a female luer connector, extension tube and clamp. The total length of the female luer connector and the extension tubing was manufactured to maximize the length and volume that would be expected to be encountered clinically. *Candida albicans* (fungus) was chosen as the challenge microorganism, because in previous tests *Candida albicans* was shown to be the most challenging microorganism for the ClearGuard HD to eradicate. *Candida albicans* were added to three different lock solutions: heparin-serum, saline-serum, and SDB broth. These solutions represent the most relevant (and challenging) solutions that would be expected clinically. The catheters were filled with the lock solutions and *Candida albicans*, next the sealing covers (either the ClearGuard HD or a standard sealing cover) were secured, and then the catheters were incubated for approximately 46 hours to simulate the time between dialysis sessions. After incubation, the sealing covers were removed and the lock solution was tested for the presence of organisms.

Figure 27:
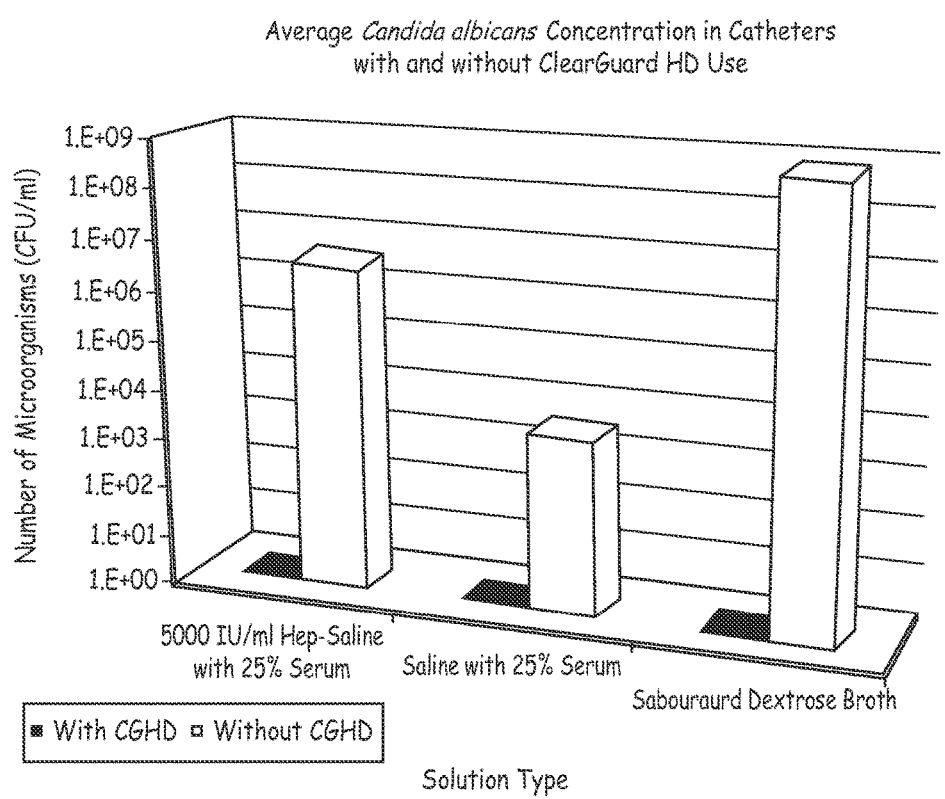
FIG. 27 shows the concentration of microbes grown in various catheter conditions.

Experiment 1 results: The organism count is shown in FIG. 27 for ClearGuard HD sealing covers and standard sealing covers (shown as "with CGHD" and "without CGHD", respectively).

| Organism Count at Study End | | | |
|---|---|---|---|
| Solution | With CGHD | Without CGHD | Organism Reduction* |
| 5000 IU/ml Hep-Saline with 25% Serum | 0.0E+00 | 3.6E+06 | 3.6E+06 |
| Saline with 25% Serum | 0.0E+00 | 3.8E+03 | 3.8E+03 |
| SDB Broth | 0.0E+00 | 7.7E+08 | 7.7E+08 |

*Actual reduction in organism count is likely higher than calculated in this test because no organisms survived in the CGHD arm of the study.

The antimicrobial effectiveness of the ClearGuard HD was assessed against *Candida albicans*, the microorganism which has been the most difficult to eradicate when tested in a clinically relevant catheter model containing the most challenging and clinically relevant fluids.

All test samples using the ClearGuard HD had complete kill of the *Candida albicans*. In comparison, all control samples demonstrated growth of the CA. Since no *Candida albicans* survived during the ClearGuard HD portion of the test, the actual *Candida albicans* reduction may be significantly higher (better) than the sensitivity of this test. The minimum reduction of *Candida albicans*, when using the ClearGuard HD in place of a standard sealing cover, was shown to be:

a. $3.6 \times 10^6$ CFU/ml for Heparin with 25% Serum
b. $3.8 \times 10^3$ CFU/ml for Saline with 25% Serum
c. $7.7 \times 10^8$ CFU/ml for SDB Broth This test demonstrates that the ClearGuard HD produces a significant reduction in *Candida albicans* within a clinically relevant catheter and with clinically relevant solutions. *Candida albicans* was previously shown to be the most difficult organism to reduce of the other clinically relevant microorganisms tested, therefore concluding that the ClearGuard HD produces broad-spectrum reduction in clinically relevant microorganisms.

Experiment 2

The objective of this experiment was to assess the relative rate of microorganism contamination in hemodialysis catheter lumens when using the ClearGuard HD versus standard sealing covers in a simulated clinical environment. This experiment was intended to examine the effectiveness of the ClearGuard HD at preventing microorganism contamination of hemodialysis catheter lumens (both proximal and distal to the extension tubing clamp), compared to standard sealing covers in a simulated clinical environment. Growth media was used inside of the catheter instead of the standard lock solution in order to provide an extremely sensitive means of detecting whether any microorganisms entered inside the catheter.

During clinical use, hemodialysis catheter hubs are routinely exposed to microorganisms because the catheter and hub lies against the patient's skin. All commercially available catheter sealing covers are primarily designed to keep fluid inside the catheter lumen but they are not well designed for preventing microorganisms from reaching and colonizing catheter lumens.

In order to compare whether the rate of microorganism colonization is affected by sealing cover type (ClearGuard HD versus standard sealing cover), twenty identical catheters were affixed to clothing, in a manner that would keep the catheters in contact with human skin, which occurs during clinical use. The catheters were kept in contact with the skin for a maximum of 26 days. Once a catheter's lumen was determined to be contaminated, the catheter was allowed to be removed from the study. The test consisted of two arms: 1) the ClearGuard HD arm, and 2) the standard sealing cover arm. Except for the sealing cover type used, the two arms were identical in all other ways (i.e., identical catheters, solutions, handling, etc.).

The study was designed to mimic the hemodialysis clinical practice as closely as practical. The entire volume of lock solution, including the solution distal to the clamp, was included in the microbiological testing to ensure with high probability that if any microorganisms were present anywhere within the catheter that they would be detected. Standard microbiological techniques were used to test for the presence of organisms.

Figure 28:
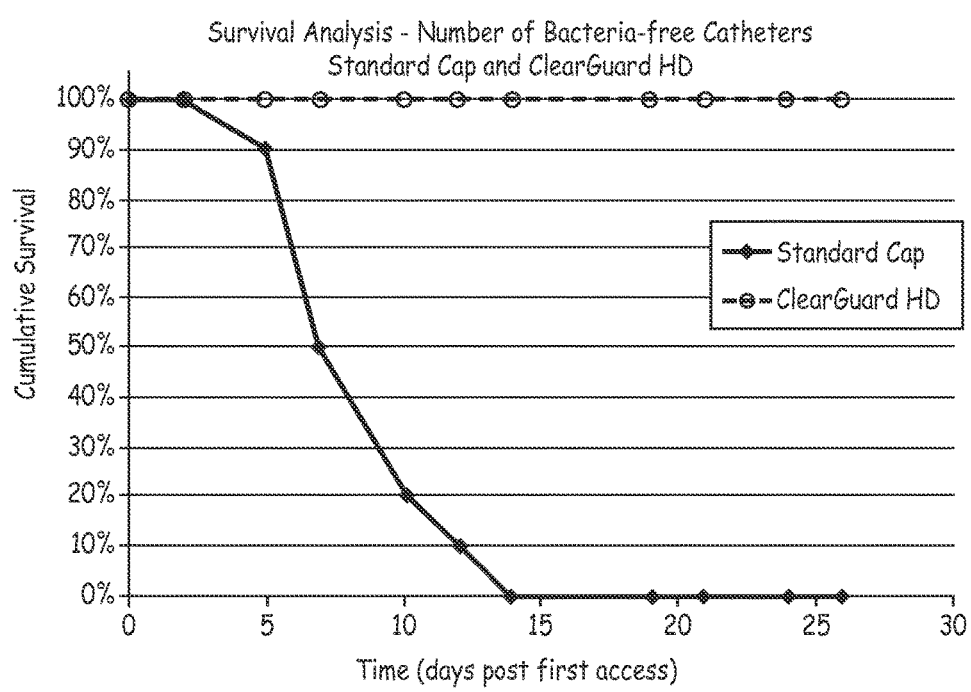
FIG. 28 shows a chart of survival analysis of bacteria-free catheters under various conditions.

The number of catheters that remained free from microorganism contamination as time progressed is illustrated in FIG. 28. Within fourteen days, all catheters using standard sealing covers had become contaminated, while none of the catheters using the ClearGuard HD had become contaminated throughout the full twenty-six days of the experiment. This experiment showed that, when catheters were filled with a growth media, were worn to simulate actual patient end use and were subjected to a standard dialysis fluid exchange schedule, the catheters using standard sealing covers became contaminated with microorganisms at a mean time to failure of 8.9 days, and all of these catheters (10 out of 10) became contaminated by 14 days. In comparison, none of the catheters using the ClearGuard HD (0 out of 10) became contaminated throughout the entire 26 day test. The ClearGuard HD performs significantly better than standard sealing covers (the current standard of care) at reducing microorganism contamination inside of catheters in a simulated clinical environment.

Experiment 3

The objective of this experiment was to confirm whether an adequate amount of antimicrobial composition elutes from the sealing cover into a catheter within an acceptable timeframe. Catheters were each filled with one of three lock solutions: sodium heparin, sodium citrate, and sodium chloride (saline). Sealing covers were then placed on the catheter hubs for the following durations: less than 10 seconds, 6 hours, 12 hours, 24 hours, 48 hours, and 72 hours. Five replicates were tested at each time point and each lock solution. At the end of the time period, the ClearGuard HDs were removed from the catheters, and the chlorhexidine that eluted into each of the catheter was measured.

Within 6 hours of the ClearGuard HD sealing cover being inserted into the catheter, the average elution was over 20 µg in all lock solutions (equating to more than 10% of the antimicrobial present on the elongate member). The amount of antimicrobial composition eluted increased with time, averaging greater than 30 µg (greater than 15% of the antimicrobial present on the elongate member) in all lock solutions at 72 hours.

This test confirmed that the sealing cover is capable of delivering an adequate amount of antimicrobial agent into a catheter within 6 hours of being inserted.

Experiment 4

The objective of this experiment was to confirm whether a sealing cover is capable of delivering more antimicrobial composition into the hub of a catheter than it delivers into the other regions of the catheter. Experiments were performed to quantify the distribution of the chlorhexidine along the length of the catheter resulting from a ClearGuard HD sealing cover being inserted into the catheter. The following test results demonstrated that the sealing cover is capable of preferentially delivering more antimicrobial agent into the hub of the catheter in comparison to the remainder of the catheter, and that this preferential distribution is substantial even after the sealing cover has been in place for 48 hours.

In this experiment, a catheter was filled with heparin saline lock solution and the catheter was clamped 96 millimeters from the proximal end face of the hub. A sealing cover was then inserted into the catheter and allowed to sit for 48 hours, representing the time that the sealing cover would commonly remain in place in a clinical setting. After the 48 hour time period elapsed, the catheter was isolated into regions using hemostats in order to allow the amount of chlorhexidine to be measured in each of the regions. The total amount of chlorhexidine present in each region was measured using HPLC, and was performed using 10 test replicates.

Figure 29:
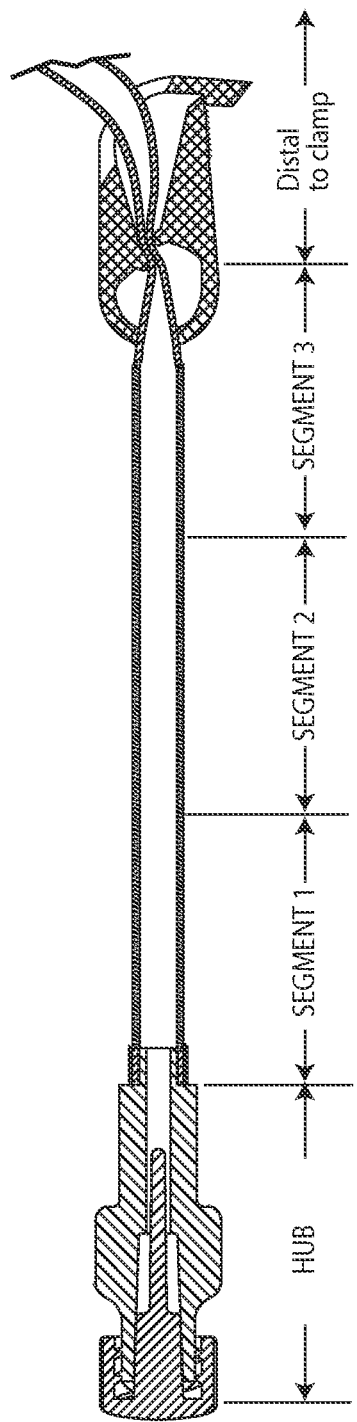
FIG. 29 is a side cross section view the proximal end of a catheter, including a cover with elongate member, hub, lumen, and a clamp.

FIG. 29 shows the location of the isolated regions. Proximal to the catheter clamp, there were four regions consisting of the hub region and three extension tubing regions (called segment 1, 2 and 3). Each of these regions was 24 mm long. These regions combined form a proximal region to the catheter. The final region was distal to the clamp, forming a distal region to the catheter. After the 48 hours, the sealing covers were removed and measurements were performed. Ten test replicates were tested and the average amount of antimicrobial in each region is presented in FIG. 30.

Figure 30:
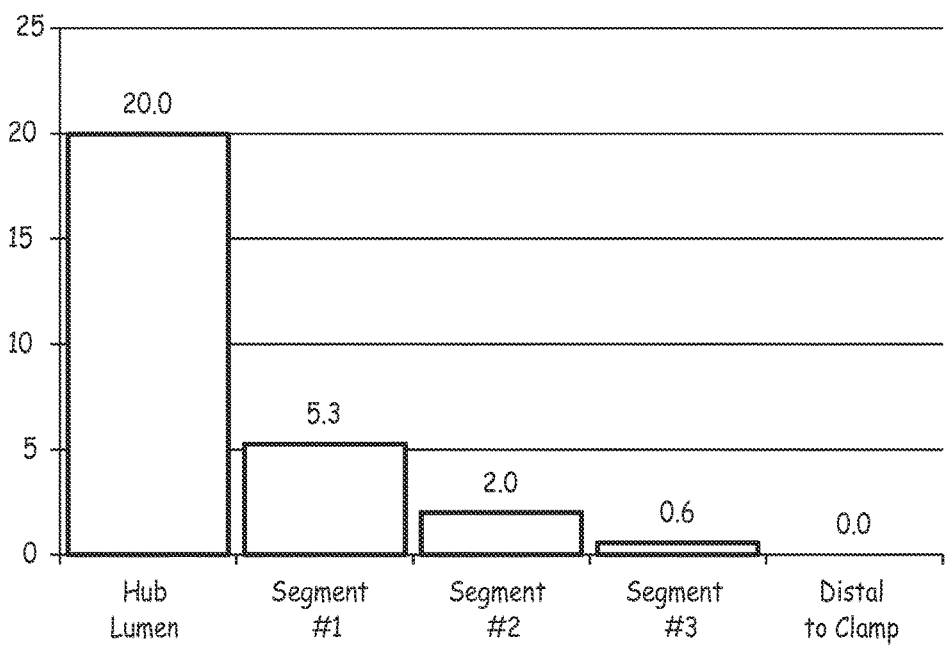
FIG. 30 is a chart showing the distribution of an antimicrobial agent within various segments of a catheter 48 hours after a cover made in accordance with an example implementation of the invention was inserted into the proximal end of the catheter.

As indicated in FIG. 30, on average approximately 28 µg of chlorhexidine had eluted into the heparin-saline lock solution, with 20 µg (72% of the eluted amount) being contained in the hub region, which is more than all other regions combined. The hub contained 0.084 mL of lock solution; therefore, the hub contained over 235 µg/mL of chlorhexidine. In comparison, segments 1, 2 and 3 each contained approximately 0.180 mL of lock solution, producing an average chlorhexidine concentration of 29, 11, and 3 µg/mL in segments 1, 2, and 3, respectively. There was initially an average of 214 µg of chlorhexidine acetate on the elongate member. Therefore approximately 13% of the antimicrobial that was originally present on the elongate member had eluted into the lock solution.

This test was repeated using sodium citrate and saline lock solutions. In all cases, the average amount of chlorhexidine in the hub exceeded 200 µg/mL, and the largest amount of antimicrobial was present in the hub, with less contained in the regions distal to the hub. In all cases, the amount of antimicrobial was substantially greater in the hub due to precipitate adhering to the walls of the catheter and the confining/flow-restricting effect of the elongate member within the hub. When heparin-saline is used as the lock solution, more than 50% of the antimicrobial composition that elutes into the lock solution precipitates onto the interior wall of the catheter.

It is desirable to have a high concentration of antimicrobial composition in the hub region, especially along the walls of the hub, in order to kill the organisms before they have a change to migrate into the distal regions of the catheter. Having no measurable antimicrobial composition distal to the clamp is also advantageous because it substantially reduces the potential for antimicrobial agent entering the patient's bloodstream.

Experiment 5

The objective of this experiment was to demonstrate that certain implementations of the sealing cover of the present invention are capable of depositing an antimicrobial composition onto the internal and external surfaces of a catheter. One of the greatest drawbacks of present day antimicrobial treated catheters is that the antimicrobial wears off quickly over time. In the case of commercially available antimicrobial catheters, within two days of use over 50% of the antimicrobial may be washed away.

In this experiment, catheters which initially contained no antimicrobial composition were used with ClearGuard HD sealing covers in a manner that was intended to simulate hemodialysis use over multiple hemodialysis sessions. Each of the catheters were filled (locked) with saline, were clamped, and new sealing covers were inserted. Each sealing cover remained on the catheter for two to three days, which is standard practice in dialysis. After the two to three day period, the sealing covers were removed and the catheters were aspirated and flushed per clinical protocol. At this point the catheters were either tested to quantify the amount of antimicrobial on the surfaces (which removed them from further simulated dialysis), or they were subjected to another use that included simulated dialysis (saline flowing the catheter at 350 mL/hour), followed by insertion of a new sealing cover for two to three days, until its removal and the catheter being aspirated and flushed. Successive rounds were continued until all of the desired time point data were gathered. Four lots of 3-5 catheters were used: one lot for each time point of 1 use, 3 uses, 5 uses and 9 uses. A new sealing cover was inserted for each catheter use, thus 90 sealing covers were used in total.

Figure 31:
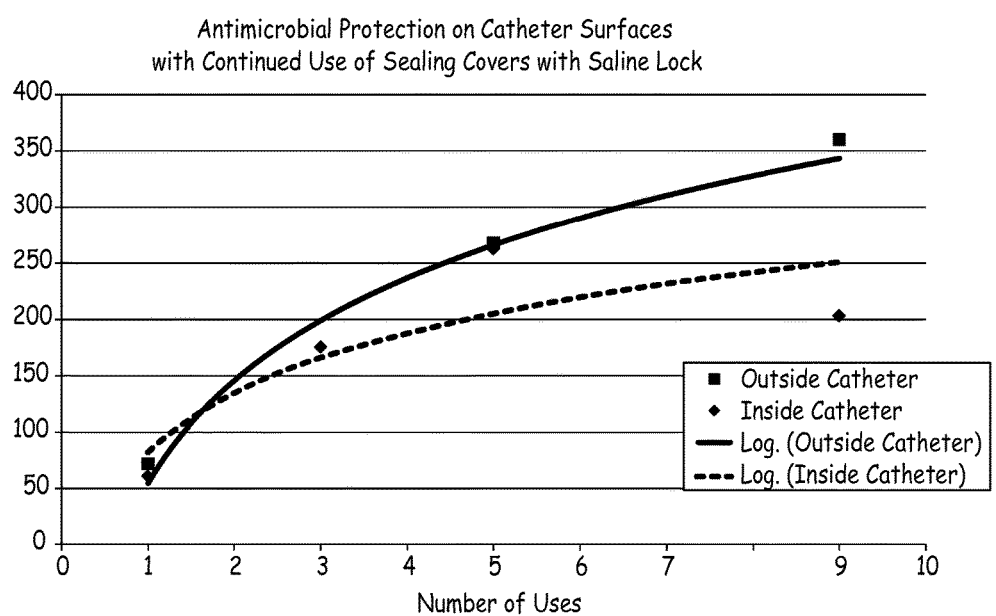
FIG. 31 is a chart showing the quantity of antimicrobial on the internal and external surfaces of a catheter at specific points in time.

The quantity of antimicrobial on the internal and external catheter surfaces was measured at the specific time points, and the results of this experiment are shown in FIG. 31. A logarithmic fit to the data was performed, showing that the sealing covers apply antimicrobial composition to the catheters and that the amount of antimicrobial composition on both the internal and external catheter surfaces increases with multiple uses, but approaches an upper limit with multiple uses. On the internal surface, the majority of the antimicrobial is contained within the hub. On the external surface the antimicrobial is contained on the proximal hub end face and the threads. The residual protection on the catheter surfaces alone is sufficient to provide substantial protection against infectious organisms. The same test was performed using heparin-saline lock solution in place of the saline lock solution; this test also demonstrated that the sealing covers apply antimicrobial composition to the catheters.

Experiment 6

The objective of this experiment was to confirm that the sealing cover of certain embodiments of the invention are capable of killing a broad spectrum of microorganisms in a clinically relevant test model. A test was designed to evaluate effectiveness at killing organisms in catheter hubs. The test was designed to simulate a scenario where the hemodialysis hub becomes challenged with microbes at the end of a dialysis session, and a sealing cover is employed to reduce or eliminate the contaminating organisms.

In addition to the test devices, control devices were used to allow for a comparison between the efficacy of the invention (test device) compared to an uncoated sealing cover (control device). Each catheter was inoculated with organisms from one of the multiple organism strains that were tested. After the catheters were inoculated, a sealing cover was inserted into each of the inoculated catheters. Three test replicates were used for each of the organism strains, in both the test and control arms. After two days of incubation (representing the time between dialysis sessions), the sealing covers were removed and microbiologic testing was performed to quantify the number of organisms remaining within each catheter. The results showed that the sealing cover of this invention produced a 4-log (10,000 fold) or greater reduction in the number of organisms in the catheter hub against each of the following organisms:

*Staphylococcus aureus*
*Staphylococcus aureus* (MRSA)
*Staphylococcus epidermidis* (MRSE)
*Enterococcus faecium* (VRE)
*Pseudomonas aeruginosa*
*Acinetobacter baumannii*
*Escherichia coli*
*Candida albicans*
*Candida paratropicalis*

The organisms in the above list account for approximately 70% of all catheter-associated bloodstream infections, and they include gram-negative bacteria, gram-positive bacteria, and fungi. Therefore, the sealing cover of this invention is effective at killing a broad range of clinically relevant organisms within a catheter.

While the invention has been particularly shown and described as referenced to the embodiments thereof, those skilled in the art will understand that the foregoing and other changes in form and detail may be made therein without departing from the spirit and scope of the invention.

What is claimed is:

1. A cap system for capping a hemodialysis catheter, the cap system comprising:
    two antimicrobial caps, each of the antimicrobial caps comprising an elongate member comprising an antimicrobial composition;
    a packaging container for securing the antimicrobial caps prior to use, the packaging container comprising a body comprising:
    a first end, the first end having a first opening leading to a first volume within the body;
    a second end, the second end having a second opening leading to a second volume within the body;
    the first and second openings configured to each hold one of the two antimicrobial caps;
    wherein the first and second openings are offset from one another.

2. The cap system of claim 1, further comprising a sealing enclosure enveloping the antimicrobial caps and packaging container prior to use.

3. The cap system of claim 1, wherein the packaging container with the antimicrobial caps installed does not readily roll.

* * * * *